US008263638B2

(12) United States Patent
Beatch et al.

(10) Patent No.: US 8,263,638 B2
(45) Date of Patent: Sep. 11, 2012

(54) DOSING REGIMENS FOR ION CHANNEL MODULATING COMPOUNDS

(75) Inventors: Gregory N Beatch, Vancouver (CA); Lilian Clohs, Saint-Laurent (CA)

(73) Assignee: Cardiome Pharma Corp., Vancouver B.C. (CA)

( * ) Notice: Subject to any disclaimer, the term of this patent is extended or adjusted under 35 U.S.C. 154(b) by 0 days.

(21) Appl. No.: 11/667,139

(22) PCT Filed: Nov. 8, 2005

(86) PCT No.: PCT/US2005/040585
§ 371 (c)(1),
(2), (4) Date: Oct. 11, 2007

(87) PCT Pub. No.: WO2006/053037
PCT Pub. Date: May 18, 2006

(65) Prior Publication Data
US 2008/0171785 A1  Jul. 17, 2008

Related U.S. Application Data

(60) Provisional application No. 60/626,328, filed on Nov. 8, 2004, provisional application No. 60/652,185, filed on Feb. 10, 2005, provisional application No. 60/676,463, filed on Apr. 29, 2005, provisional application No. 60/702,873, filed on Jul. 27, 2005, provisional application No. 60/729,387, filed on Oct. 21, 2005.

(51) Int. Cl.
*A01N 43/36* (2006.01)
*A61K 31/40* (2006.01)

(52) U.S. Cl. ........................................ 514/424

(58) Field of Classification Search ............... None
See application file for complete search history.

(56) References Cited

U.S. PATENT DOCUMENTS

| | | | |
|---|---|---|---|
| 2,954,380 A | 9/1960 | Shapiro et al. | 260/268 |
| 3,218,328 A | 11/1965 | Shapiro et al. | 260/294 |
| 4,145,435 A | 3/1979 | Szmuszkovicz | 424/274 |
| 4,179,501 A | 12/1979 | Szmuszkovicz | 424/226 |
| 4,598,087 A | 7/1986 | Horwell | 514/429 |
| 4,656,182 A | 4/1987 | Horwell | 514/324 |
| 4,663,343 A | 5/1987 | Horwell et al. | 514/429 |
| 4,855,316 A | 8/1989 | Horwell et al. | 514/422 |
| 4,880,800 A | 11/1989 | Wallis et al. | 514/211 |
| 4,906,655 A | 3/1990 | Horwell et al. | 514/422 |
| 5,019,588 A | 5/1991 | Horwell et al. | 514/409 |
| 5,051,428 A | 9/1991 | Horwell et al. | 514/320 |
| 5,059,620 A | 10/1991 | Stout et al. | 514/422 |
| 5,492,825 A | 2/1996 | Jan et al. | 435/240.2 |
| 5,506,257 A | 4/1996 | MacLeod et al. | 514/422 |
| 5,637,583 A | 6/1997 | MacLeod et al. | 514/212 |
| 5,670,335 A | 9/1997 | Jan et al. | 435/29 |
| 5,728,535 A | 3/1998 | Lester et al. | 435/7.2 |
| 5,734,021 A | 3/1998 | Lester et al. | 530/350 |
| 5,750,537 A | 5/1998 | Nomura et al. | 514/304 |
| 5,817,698 A | 10/1998 | Brown et al. | 514/646 |
| 5,885,984 A | 3/1999 | MacLeod et al. | 514/211 |
| 6,174,879 B1 | 1/2001 | MacLeod et al. | 514/212.01 |
| 6,180,632 B1 | 1/2001 | Myers et al. | 514/252.1 |
| 6,210,809 B1 | 4/2001 | Okutomi et al. | 428/546 |
| 6,214,809 B1 | 4/2001 | Fermini et al. | 514/75 |
| 6,214,810 B1 | 4/2001 | Fermini et al. | 514/75 |
| 6,451,819 B2 | 9/2002 | Alanine et al. | 514/326 |
| 6,521,619 B2 | 2/2003 | Link et al. | 514/237.2 |
| 6,649,603 B2 | 11/2003 | Sum | 514/210.01 |
| 6,979,685 B1 | 12/2005 | Beatch et al. | 514/231.2 |
| 7,053,087 B1 | 5/2006 | Beatch et al. | 514/237.8 |
| 7,057,053 B2 | 6/2006 | Beatch et al. | 548/541 |
| 7,101,877 B2 | 9/2006 | Bain et al. | 514/231.2 |
| 7,259,184 B2 | 8/2007 | Beatch et al. | 514/424 |
| 7,345,086 B2 | 3/2008 | Beatch et al. | 514/424 |
| 7,345,087 B2 | 3/2008 | Beatch et al. | 514/424 |
| 7,507,545 B2 | 3/2009 | Fedida et al. | 435/7.2 |
| 7,524,879 B2 | 4/2009 | Beatch et al. | 514/424 |
| 7,534,790 B2 | 5/2009 | Bain et al. | 514/231.2 |
| 2005/0038256 A1 | 2/2005 | Barrett et al. | 546/236 |
| 2005/0070552 A1 | 3/2005 | Fedida et al. | 514/255.06 |
| 2006/0252753 A1 | 11/2006 | Beatch et al. | 514/237.8 |
| 2007/0004718 A1 | 1/2007 | Bain et al. | 514/232.2 |
| 2007/0099983 A1 | 5/2007 | Barrett et al. | 514/408 |
| 2007/0190156 A1 | 8/2007 | Beatch et al. | 424/489 |
| 2007/0197632 A1 | 8/2007 | Beatch et al. | 514/327 |
| 2007/0254945 A1 | 11/2007 | Jung et al. | 514/424 |
| 2008/0188547 A1 | 8/2008 | Beatch et al. | 514/424 |
| 2009/0041841 A1 | 2/2009 | Beatch et al. | 424/465 |

FOREIGN PATENT DOCUMENTS

| | | |
|---|---|---|
| CA | 1234808 | 4/1988 |
| CA | 1235122 | 4/1988 |
| CA | 2004575 | 6/1990 |
| CA | 2058502 | 6/1993 |
| CA | 2172513 | 3/1995 |
| CA | 2240728 | 3/1997 |
| CA | 2244209 A1 | 7/1997 |
| CA | 2008391 | 12/1997 |

(Continued)

OTHER PUBLICATIONS

Han (Advances in Characterization of Pharmaceutical Hydrates. Trends in Bio/Pharmaceutical Industry, pp. 25-29. Mar. 2006).*
Vippagunta et al (Adv Drug Deliv Rev 48:3-26, 2001).*
Billman (Curr Op Invest Drugs 4:352-354, 2003).*
Cardiome Press Release (dated Jan. 17, 2002).*
Cardiome RSD-1235 Fact Sheet (dated Oct. 1, 2002).*
Billman, George E., "RSD-1235 Cardime," Current Opinion in Investigational Drugs (Thomas Current Drugs) 4(3): 352-354, 2003.
Roy, Denis, et al., "A Randomized, Controlled Trial of RSD1235, a Novel Anti-Arrhytmic Agent, in the Treatment of Rcent Onset Atrial Fibrillation," Journal of the American College of Cardiology 44(12): 2355-2361, 2004.
STN Online, File Registry RN=748810-28-8, Sep. 21, 2004.
Adcock et al., "RSD931, a novel anti-tussive agent acting on airway sensory nerves," *Br J Pharm* 138(3):407-416, 2003.
Altria et al., "Capillary Electrophoresis as a Routine Analytical Tool in Pharmaceutical Analysis," *LCGC* 19(9): 972-985, Sep. 2001.
Amin et al., "RPR 101821, a New Potent Cholesterol-lowering Agent: Inhibition of Squalene Synthase and 7-Dehydrocholesterol Reductase," *Naunyn-Schmiedeberg's Arch Pharmacol* 353:233-240, 1996.

(Continued)

*Primary Examiner* — Craig Ricci

(57) ABSTRACT

Dosing regimens, routes of administration and methods for the treatment or prevention of arrhythmias are disclosed. In these methods, arrythmias (e.g. atrial fibrillation, atrial flutter, early after depolarizations and prolongation of QT interval) may be reduced or eliminated by administering ion channel modulating compounds to a subject in need thereof via the dosing regimens disclosed herein.

12 Claims, 8 Drawing Sheets

FOREIGN PATENT DOCUMENTS

| | | |
|---|---|---|
| CA | 2289055 | 1/1999 |
| CA | 2268590 | 10/2000 |
| CA | 2132841 | 3/2001 |
| DE | 2 259 260 | 6/1974 |
| DE | 2 658 401 | 7/1978 |
| DE | 3 517 901 | 12/1985 |
| EP | 222533 A1 | 5/1987 |
| EP | 147085 A2 | 3/1990 |
| EP | 147085 B1 | 3/1990 |
| EP | 372466 A2 | 6/1990 |
| EP | 372466 A3 | 6/1990 |
| EP | 380063 A1 | 8/1990 |
| EP | 380063 B1 | 8/1990 |
| EP | 552386 A1 | 7/1993 |
| EP | 720605 B1 | 7/1996 |
| HU | 215963 B | 2/1995 |
| JP | 02-270864 | 11/1990 |
| WO | WO 93/19056 | 9/1993 |
| WO | WO 94/07843 | 4/1994 |
| WO | WO 94/14435 | 7/1994 |
| WO | WO 95/08544 | 3/1995 |
| WO | WO 95/28155 | 10/1995 |
| WO | WO 96/18615 | 6/1996 |
| WO | WO 96/23894 | 8/1996 |
| WO | WO 97/32857 | 9/1997 |
| WO | WO 97/49680 | 12/1997 |
| WO | WO 99/02159 | 1/1999 |
| WO | WO 99/03468 | 1/1999 |
| WO | WO 99/11252 | 3/1999 |
| WO | WO 99/16431 | 4/1999 |
| WO | WO 99/50205 | 10/1999 |
| WO | WO 99/50225 * | 10/1999 |
| WO | WO 00/47547 | 8/2000 |
| WO | WO 00/51981 | 9/2000 |
| WO | WO 01/96335 | 12/2001 |
| WO | WO 03/105756 | 12/2003 |
| WO | WO 2004/008103 | 1/2004 |
| WO | WO 2004/098525 * | 11/2004 |
| WO | WO 2004/099137 | 11/2004 |
| WO | WO 2005/018635 | 3/2005 |

OTHER PUBLICATIONS

Alzheimer's Disease Information Page [online], [retrieved on Oct. 3, 2006]. Retrieved from the Internet, URL: <http://www.ninds.nih.gov/disorders/alzheimersdisease/alzheimersdisease.htm>.

Bain, et al., "Ion Channel Modulating Compounds and Uses Thereof," U.S. Appl. No. 09/283,873, filed Mar. 31, 1999.

Bain, et al., "Ion Channel Modulating Compounds and Uses Thereof," U.S. Appl. No. 09/680,988, filed Oct. 6, 2000.

Bain, et al., "Ion Channel Modulating Compounds and Uses Thereof," U.S. Appl. No. 12/424,450, filed Apr. 15, 2009.

Bain et al., "Better Antiarrhythmics? Development of Antiarrhythmic Drugs Selective for Ischaemia-Dependent Arrhythmias," *Drug Development Research* 42:198-210, 1997.

Barrett and Walker, "Glibenclamide Possesses Transient, Ischaemia Selective Class III Antiarrhythmic Actions But Does Not Prevent Ischaemic Arrhythmias," *BPS Proceedings* 116P, 1996.

Barrett et al., "A Model of Myocardial Ischemia for the Simultaneous Assessment of Electrophysiological Changes and Arrhythmias in Intact Rabbits," *J Pharmacol Toxicol Methods* 37(1):27-36, 1997.

Barrett et al., "Ischaemia selectivity confers efficacy for suppression of ischaemia-induced arrhythmias in rats," *Eur J Pharm* 398:365-374, 2000.

Barrett et al., "Atypical Dose Response Curves for Antiarrhythmic Drugs," *BPS Proceedings* 115P, 1996.

Barrett, "Ischemia Selective Electrophysiological and Antiarrhythmic Actions of RSD1019 in Ischemic Cardiac Tissue," *J Mol Cell Cardiol* 29:197, 1997.

Barrett et al., "RSD1019 suppresses ischaemia-induced monophasic action potential shortening and arrhythmias in anaesthetized rabbits," *Br J Pharm* 131(3):405-414, 2000.

Beatch et al., "Aminocyclohexyl Ether Compounds and Uses Thereof," U.S. Appl. No. 10/977,343, filed Oct. 29, 2004.

Beatch et al., "Aminocyclohexyl Ether Compounds and Uses Thereof," U.S. Appl. No. 11/201,776, filed Aug. 11, 2005.

Beatch et al., "Ion Channel Modulating Compounds and Uses Thereof," U.S. Appl. No. 12/412,010, filed Mar. 26, 2009.

Beatch et al., "RSD1235 Selectively Prolongs Atrial Refractoriness and Terminates AF in Dogs with Electrically Remodelled Atria," *Pharmacologist* 44(2) (Supp I), A15: XIV$^{th}$ World Congress of Pharmacology: Meeting Abstracts, 2002. Abstract No. 22.11.

Beatch et al., "Effect of a Novel Anti-tussive Compound CP1 Against Citric Acid Induced Cough in Guinea-Pigs," *Proc West Pharmacol Soc* 44:252, 2001.

Beatch et al., "RSD1235 Rapidly and Effectively Terminates Atrial Fibrillation," Abstract submission ESC Congress Aug. 30-Sep. 3, 2003, in Vienna, Austria.

Beatch et al., "RSD1235, A Novel Atrial-Selective Antiarrhythmic Drug, Shows Rapid and Extensive Oral Absorption in Man," 12$^{th}$ International Congress on Cardiovascular Pharmacotherapy, May 7-10, 2003, Barcelona, Spain.

Beatch et al., "Ventricular Fibrillation, an Uncontrolled Arrhythmia Seeking New Targets," *Drug Develop Res* 55:45-52, 2002.

Beatch, "Antihistamine-induced Ventricular Arrhythmias," *BPS Proceedings* 120P, 1996.

Beatch et al., "Characterization of a Non-Human Primate Model of Drug-Induced Torsades De Pointes," *Proc West Pharmacol Soc* 40:13-16, 1997.

Beatch et al., "RSD1235 Selectively Prolongs Atrial Refractoriness and Terminates AF in Dogs with Electrically Remodelled Atria," *PACE* 24(Part II):698. Abstract 702, May 10, 2002.

Bian et al., "Effects of Kappa-opioid receptor stimulation in the heart and the involvement of protein kinase C," Brit J Pharm 124:600-606, 1998.

Boiadjiev and Lightner, "pH-Sensitive Exciton Chirality Chromophore. Solvatochromic Effects on Circular Dichroism Spectra," *Tetrahedron: Asymmetry* 7(10):2825-2832, 1996.

Bowen et al., "Characterization of the Enantiomers of cis-N[2-(3,4-Dichloropheny)Ethyl]-N-Methy1-2-(1-Pyrrolidinyl)Cyclohexylamine (BD737 and BD738): Novel Compounds with High Affinity, Selectivity and Biological Efficacy at Sigma Receptors," *J Pharmacol Exp Ther* 262(1):32-40, 1992.

Cardiome Pharma Corp. (Jan. 31, 2001). "Nortran Drug Effective in Atrial Arrhythmia Model" (http://cardiome.com/wordpress/?p=104). Press Release.

Cardiome Pharma Corp. (Jun. 21, 2001). "Nortran Antiarrhythmia Drug Demonstrates Oral Bioavailability" (http://cardiome.com/wordpress/?p=99). Press Release.

Cardiome Pharma Corp. (Jul. 30, 2001). "Cardiome Pharma Completes Phase I Safety Study" (http://cardiome.com/wordpress/?p=97). Press Release.

Cardiome Pharma Corp. (Sep. 3, 2002). "Cardiome Drug Effective for Heart Patients" (http://cardiome.com/wordpress/?p=75). Press Release.

Cardiome Pharma Corp. (Dec. 5, 2002). "Cardiome Reports Oral Absorption of RSD1235 in Humans" (http://cardiome.com/wordpress/?p=72). Press Release.

Cardiome Pharma Corp. (Dec. 20, 2004). "Cardiome's Pivotal AF Study Achieves Primary Endpoint" (http://cardiome.com/wordpress/?p=14). Press Release.

Cardiome Pharma Corp. (Feb. 4, 2005). "Cardiome Reports Additional ACT 1 Clinical Results" (http://cardiome.com/wordpress/?p=2). Press Release.

Cardiome Pharma Corp. (Apr. 25, 2005). "Cardiome Successfully Completes Second Phase 1 Trial" (http://cardiome.com/wordpress/?p=230). Press Release.

Cardiome Pharma Corp. (Aug. 31, 2005). "Cardiome Successfully Completes RSD1235 Oral Phase 1 Trial" (http://cardiome.com/wordpress/?p=255). Press Release.

Cardiome Pharma Corp. (Sep. 29, 2005). "Cardiome and Astellas Announce Positive Results from Second Phase 3 Trial" (http://cardiome.com/wordpress/?p=262). Press Release.

Cardiome Pharma Corp. (May 5, 2006). "Cardiome Reports Additional Phase 1 Trial Data for Oral RSD1235" (http://cardiome.com/wordpress/?p=291). Press Release.

Cardiome Pharma Corp. (Jul. 24, 2006). "Cardiome Announces Interim Phase 2A Results for Oral RSD1235" (http://cardiome.com/wordpress/?p=312). Press Release.

Cardiome Pharma Corp. (Sep. 13, 2006). "Cardiome Announces Positive Phase 2A Results for Oral RSD1235" (http://cardiome.com/wordpress/?p=321). Press Release.
Cardiome Pharma Corp. Healthcare (Underweight) Company Report Dec. 12, 2002. 26 pages.
Clohs and Wong, "Validation of a capillary electrophoresis assay for assessing the metabolic stability of verapamil in human liver microsomes," *J Cap Elec & Microchip Tech* 007(5/6):113-117, 2002.
Clohs, "Capillary Electrophoresis and Its Applications in The Pharmaceutical Industry—Short Course: One Platform Fits Many Applications," CSC 2002, 52 pages.
Clohs, "Capillary Electrophoresis as an Analytical Tool in the Drug Discovery Process," Presentation CE Symposium, Aug. 2000, 40 pages.
Clohs, "The Versatility of CE for Drug Pharmacokinetics and Metabolism Studies," CE in the Biotechnology & Pharmaceutical Industries (Symposium), Boston, Aug. 2001, 46 pages.
Clohs, "Pharmacokinetics profiling of new drug candidates: a key process in drug discovery," *Beckman Coulter P/ACE Setter* 4(1):Jun. 6, 2000.
Clohs and Winstanley, "CE Analysis of Propranolol in Human Serum Using Dynamic Capillary Coating," *CE Currents: LCGC Europe*, Reader Service 14, pp. 289-293, May 2002.
Clohs, "Bio-Analytical Applications of Capillary Electrophoresis in a Drug Discovery Setting," CSC Seminar, Jun. 5, 2002, 29 pages.
Clohs, "CE and Drug Metabolism Studies: A Powerful Combination in Drug Discovery," CE in the Biotechnology and Pharmaceutical Industries (Symposium), Washington, DC, Aug. 2002, 31 pages.
Crotti et al., "Regiochemical control of the ring-opening of epoxides by means of chelating processes Part 13 . . . ," *Chemical Abstracts* 129(17):662-663, Abstract No. 216472k, 1998.
Crotti et al., "Synthesis and Ring-Opening Reactions of the Diastereoisomeric cis- and trans-Epoxides Derived from 3-(Benzyloxy)cyclopentene and 2-(Benzyloxy)-2,5-dihydrofuran," *Eur J Org Chem* 8:1675-1686, 1998.
De Costa et al., "Synthesis and Evaluation of N-Substituted cis-N-Methyl-2-(1-pyrrolidinyl)cyclohexylamines as High Affinity σ Receptor Ligands. Identification of a New Class of Highly Potent and Selective σ Receptor Probes," *J Med Chem* 33:3100-3110, 1990.
Doci et al., "Local Anesthetic Effects of Intradermal RSD921 in Healthy Subjects," Proceedings of the 100th Annual Meeting of the American Society for Clinical Pharmacology and Therapeutics, San Antonio, Texas, Mar. 18-20, 1999, Abstract PIII-2 in *Clin Pharm & Therap* 65(2):177, Feb. 1999.
Duan et al., "Potassium Channel Blocking Properties of Propafenone in Rabbit Atrial Myocytes," *J Pharm Exp Ther* 264(3): 1113-1123, 1993.
Ezrin et al., "Safety and Pharmacokinetics of RSD1235, a Novel Atrial Fibrillation Converting Drug, in Healthy Volunteers," Abstracts: 11th Int. Congress Cardiovasc. Pharmacother. 16 Abstract P297, 2002.
Ezrin et al., "A Dose-Ranging Study of RSD1235, A Novel Antiarrhythmic Agent, in Healthy Volunteers," Pharmacologist, 44(2) (Supplement I), A15: XIVth World Congress of Pharmacology: Meeting Abstracts, 2002. Abstract No. 22.10.
Fedida et al., " Kv1.5 is an Important Component of Repolarizing K[+]Current in Canine Atrial Myocytes," Circulation Research Peer Review Plus Manuscript PDF, 38 pages, 2002.
Fedida et al. "Kv1.5 Channels Contribute to Canine Atrial Repolarization," Circulation 2003 in press, (accepted for presentation at AHA Scientific Sessions, Nov. 8-12, 2003, Orlando, FL). Circulation 2003, v108, p1386.
Franciosi et al., "Phase II Clinical Trial of RSD921 as a Local Anaesthetic in Patients Undergoing Venous Cannulation for Elective Treatment," in Proceedings of the 28th Annual ACCP Meeting Abstract 32, p. 977, Feb. 2000.
Franciosi and McLarnon, "pH-dependent blocking actions of three novel antiarrhythmic compounds on K[+]and Na[+]currents in rat ventricular myocytes," *Eur J Pharm* 425:95-107, 2001.
Franciosi et al., "Development and evaluation of a quality assessment instrument for clinical trial protocols," *Pharmacologist* 44(2):A160, 2002.

Franqueza et al., "Effects of propafenone and 5-hydroxypropafenone on hKv1.5 channels," *Br J Pharm* 125:969-978, 1998.
Friess et al., "Central Activity Evoked in the Cat by Cis-Trans Isomers of 1,2-Aminocyclohexanol Derivatives," *Taxicol Appl Pharmacol* 3:638-653, 1961.
Grant, "Mechanisms of Atrial Fibrillation and Action of Drugs Used in its Management," *Am J Cardiol* 82:43N-49N, Oct. 16, 1998.
Halfpenny et al., "Highly Selective k-Opioid Analgesics. 3. Synthesis and Structure-Activity Relationships of Novel N-[2-(1-Pyrrolidinyl)-4- or -5-substituted-cyclohexyl]arylacetamide Derivatives", *J Med Chem* 33:286-291, 1990.
Halfpenny et al., "Highly Selective k-Opioid Analgesics. 2. Synthesis and Structure-Activity Relationships of Novel N-[(2-Aminocyclohexyl)aryl]acetamide Derivatives", *J Med Chem* 32:1620-1626, 1989.
Hanson, "Protecting Groups in Organic Synthesis," Blackwell (1999), 130 pages, pp. 10-11 provided.
Hayes et al., "RSD 992 Enhances Erection and Copulation in Rats and Erection in Primates", *Int J Impotence Res* p. 189 (Abstract P24), 1996.
Hayes et al., "Actions of Arylpiperazines on Corpus Cavernosum Smooth Muscle in Vitro", *Asia Pac J Pharmacol* 12:97-103, 1997.
Hayes et al., "Direct Actions of Arylpiperazines on Rabbit and Human Corpus Caversonal Smooth Muscle in Vitro", *Asia Pac J Pharmacol*, Abstract S15, 1997.
Hesketh et al., "Safety of RSD1235 in a rabbit Purkinje fiber model", in Proceedings of the XIVth World Congress of Phar. Meeting, Abstract No. 22.12, 2002.
Hesketh et al., "Ionic mechanisms of atrial fibrillation," *Cardiac Drug Development Guide*, ed. Pugsley, M. Ch 9, pp. 163-174, Humana Press, NJ 2003.
Keefe et al., "New Antiarrhythmic Drugs: Their Place in Therapy", *Drugs* 22:363-400, 1981.
Kertesz et al., "The Electrophysiological and Antiarrhythmic Actions of RSD Analogs of U50,488H in Rats", in Proceedings of the West Pharmacol Soc. 9 pages, 1994.
Lang et al., "Clinical Evaluation of RSD921 As a Local Anaesthetic in Patients Undergoing Venous Cannulation for Elective Treatment", *Clin Pharm & Therapeutics*, p. 142, Feb. 2000. Abstract PIII-1.
Lewis et al., "Enzyme inhibition during the conversion of squalene to cholesterol", *Steroids* 60:475-483, Jul. 1995.
Li et al., "Adrenergic Modulation of Ultrarapid Delayed Rectifier K[+]Current in Human Atrial Myocytes", *Circ Res* 78(5):903-915, May 1996.
Malayev et al., "Mechanism of Clofilium Block of the Human Kv1.5 Delayed Rectifier Potassium Channel", *Mol Pharm* 47:198-205, 1995.
Martens et al., "Einfache Synthese neuer anellierter Pyrrole", *J Synth Org Chem* 12:965-967, Dec. 1989.
Matyus et al., "Antiarrhythmic Agents: Current Status and Perspectives", *Medicinal Research Reviews* 17(5):427-451, 1997.
McLarnon et al., "Mixed Block of K[+]and Na[+]Currents by KC8851, A Structural Analogue of Tedisamil in Vitro and in Vivo Studies", *BPS Proceedings* 114P, 1996.
Moorman et al., "pK$_a$ Does Not Predict pH Potentiation of Sodium Channel Blockade by Lidocaine and W6211 in Guinea Pig Ventricular Myocardium", *The Journal of Pharmacology and Experimental Therapeutics* 238(1):159-166, 1986.
Morisawa et al., "Preparation of fluorocarbocyclic nucleosides as antitumor agents", Chemical Abstracts 115(5):904-905, abstract No. 50215n, 1991.
Nakashima et al., "Angiotensin II Type I Receptor Antagonist Prevents the Promotion of Atrial Fibrillation", *PACE* 24(Part II):698, May 10, 2002. Abstract 701.
Nattel et al., "Effects of the novel antiarrhythmic agent azimilide on experimental atrial fibrillation and atrial electrophysiologic properties", *Cardiovascular Research* 37:627-635, 1998.
Nattel et al., "RSD1235: a novel antiarrhythmic agent with a unique electrophysiological profile that terminates AF in dogs", *Eur Heart J* 22(Suppl):448 (Abstract P2362), 2001.
Nattel, "Experimental evidence for proarrhytmic mechanisms of antiarrhythmic drugs", *Cardiovascular Research* 37:567-577, 1998.

Nattel et al., "The Role of Channel Opening in Transient Outward Current Block by Quinidine, Flecainide, and 4-Aminopyridine in Human Atrial Myocytes", K Channels II: Regulation and Block, Abstract No. Tu-Pos403, 1994.

Nishi et al., "Studies on 2-Oxoquinoline Derivatives as Blood Platelet Aggregation Inhibitors. IV. Synthesis and Biological Activity of the Metabolites of 6-[4-(1-Cyclohexyl-1H-5-tetrazolyl)butoxy]-2-oxo-1,2,3,4-tetrahydroquinoline (OPC-13013)", Chem Pharm Bull 33(3):1140-1147, 1985.

Orth et al., "Cyclopentane-l-amines", Chemical Abstracts 89(15):555, Abstract No. 129113f, 1978.

Orth et al., "The Novel AF Conversion Agent RSD1235 Preferentially Blocks a Late Component of the Human Heart (hH1) $Na^+$ Current Active During Repolarization", EP Abstracts Oct. 3, 2003.

Plouvier et al., "Synthesis and Structure Activity Relationships of a Series of 2-Aminocyclohexyl . . . as Potential Ischaemia Selective Ventricular Antiarrhythmics", BMPS 994, (2002).

Pratt, et al., Oral vernakalant (RSD 1235-SR) prevents recurrence of atrial fibrillation following cardioversion, poster presented at the 2007 Heart Rhythm Society Annual Meeting (2007).

Pugsley and Goldin, "Molecular analysis of the $Na^+$ channel blocking actions of the novel class I antiarrhythmic", Br J Pharm 127:9-18, 1999.

Pugsley et al., "A Characterization of the Antiarrhythmic and Electrophysiological Properties of RSD992, A Novel Arylpiperazine Drug", XIVth World Congress of Pharmacology: Meeting Abstract 22.8, in Pharmacologist 44(2, Supp 1):A15, 2002.

Pugsley et al., "Electropharmacology of Two New Class 1 agents", Heart and Stroke Annual Conference, p. 12, 1995.

Pugsley et al., "Sodium Channel-Blocking Properties of Spiradoline, a Kappa Receptor Agonist, are Responsible for Its Antiarrhythmic Action in the Rat", J Cardiovas Pharmacol 32:863-874, 1998.

Pugsley et al., "Are the arrhythmias due to myocardial ischaemia and infarction dependent upon the sympathetic system?", Cardiol Res 43:830-831, 1999.

Ribeiro et al., "Determination of RSD921 in human plasma by high-performance liquid chromatography-tandem mass spectrometry using tri-deuterated RSD921 as internal standard: application to a phase I clinical trial", J Mass Spectrom 36:1133-1139, 2001.

Rich et al., "Quinidine Block of the Human Cardiac hKv1.5 Channel in Inside-Out Patches, K Channels II: Regulation and Block", Abstract No. Tu-Pos404, p. A209, 1999.

Roden and George, "The Cardiac Ion Channels: Relevance to Management of Arrhythmias", Annu Rev Med 47:135-148, 1996.

Roy et al., "RSD1235 Rapidly and Effectively Terminates Atrial Fibrillation", Eur Heart J, p. 3699, 2003.

Rynbrandt et al., "Cis-1-[2-(p-Anisidinomethyl)cyclohexyl]piperidine and Related Compounds. Oral Hypoglycemic Agents", J Med Chem 14(10): 985-987, 1971.

Sandro, et al. "Low pKa Predicts Antiarrhythmic Efficacy in a Series of Amino cyclohexyl Esters," Journal of Molecular and Cellular Cardiology 29(6):057, 1997.

Sanguinetti, "Modulation of Potassium Channels by Antiarrhythmic and Antihypertensive Drugs", Hypertension 19(3):228-236, Mar. 1992.

Shiroshita-Takeshita, et al., "Differential Efficacy of Drugs with Antioxidant Properties on Atrial Fibrillation Promotion by Atrial Tachycardia Remodeling in Dogs," Circulation 108(17):699, 2003.

Singh, "Antiarrhythmic Drugs: A Reorientation in Light of Recent Developments in the Control of Disorders of Rhythm", Am J Cardiol 81(6A):3D-13D, Mar. 19, 1998.

Singh, "Atrial Fibrillation: Epidemiologic Considerations and Rationale for Conversion and Maintenance of Sinus Rhythm", J Cardiovasc Pharmacol Therapeut 8(Supp 1):S13-S26, 2003.

Snyders et al., "A Rapidly Activating and Slowly Inactivating Potassium Channel Cloned from Human Heart", J. Gen. Physiol. 101:513-543, Apr. 1993.

Snyders and Yeola, "Determinants of Antiarrhythmic Drug Action—Electrostatic and Hydrophobic Components of Block of the Human Cardiac hKv1.5 Channel", Circ Res 77(3):575-583, Sep. 1995.

Srilatha et al., "Alterations in Rabbit Corpus Cavernosal Pharmacology by High Cholesterol Diet", Asia Pac J Pharmacol, Abstract S15, 1997.

Steinbeck, "Proarrhythmische Wirkungen von Antiarrhythmika—Theoretische und Klinische Aspekte", Z Kardiol 81(Supp 4):139-143, 1992.

Stevenson, Atrial Fibrillation and Heart Failure—Five More Years, N Engl J Med 351(23):2437-2440, Dec. 2, 2004.

Tong et al., "Determination of an arylether antiarrhythmic and its N-dealkyl metabolite in rat plasma and hepatic microsomal incubates using liquid chromatography-tandem mass spectrometry", J Chromatog B 759:259-266, 2001.

Tong, et al., "In Vitro Investigation of the Hepatic Extraction of RSD1070, A Novel Antiarrhythmic Compound," J Pharm Pharmaceut Sci 4(1):15-23, 2001.

Valenzuela et al., "Comparative effects of nonsedating histamine $H_1$ receptor antagonists, ebastine and terfenadine, on human Kv1.5 channels", Eur J Pharm 326:257-263, 1997.

Valenzuela et al., "Effects of Ropivacaine on a Potassium Channel (hKv1.5) Cloned from Human Ventricle", Anesthesiology 86:718-728, 1997.

Walker, "Antiarrhythmic Drug Development—Illusion and Disillusion?", Drug Develop Res 55:1-2, 2002.

Walker et al., "Determination of an arylacetamide antiarrhythmic in rat blood and tissues using reversed-phase high-performance liquid chromatography", J Chromatog B 675:257-263, 1996.

Walker et al., "Increased Electrophysiological Activity in Raised $K^+$ and low pH Improves Antiarrhythmic Efficacy for a Group of Morpholinocyclohexyl Derivatives", BPS Proceedings 118P, 1996.

Walker and Guppy, "Targeting Ischemic Ventricular Arrhythmias", Cardiac Drug Development Guide, Humana Press Inc., Totowa, NJ, pp. 175-201, 2003.

Wang et al., "Effects of Flecainide, Quinidine, and 4-Aminopyridine on Transient Outward and Ultrarapid Delayed Rectifier Currents in Human Atrial Myocytes", J Pharm Exp Ther 272(1):184-196, 1995.

Wang et al., "Sustained Depolarization-Induced Outward Current in Human Atrial Myocytes", Circ Res 73(6):1061-1076, Dec. 1993.

Wat et al., "Effects of Arylbenzacetamides on Neuromuscular Preparation", Proc West Pharmacol Soc 1994.

Wolf et al., "Impact of Atrial Fibrillation on Mortality, Stroke, and Medical Costs", Arch Intern Med 158: 229-234, Feb. 9, 1998.

Wong and Clohs, "Protein Binding Study of AA5, a New Antiarrhythmic Drug", Nortran Pharmaceuticals Inc., Vancouver, BC, Poster Conference, Aug. 2000.

Wong and Clohs, "Capillary Electrophoresis Assay to Assess in Vitro Metabolic Stability of Novel Compounds in Human Liver Microsomes", Cardiome Pharma Corp., Vancouver, BC, AAPS Poster, Oct. 2001.

Yeola et al., "Molecular Analysis of a Binding Site for Quinidine in a Human Cardiac Delayed Rectifier $K^+$ Channel"—Role of S6 in Antiarrhythmic Drug Binding, Circ Res 78(6): 1105-1114, Jun. 1996.

Yong et al., "RSD1000: A Novel Antiarrhythmic Agent with Increased Potency Under Acidic and High-Potassium Conditions", J Pharm Exp Ther 289(1):236-244, 1999.

Yong et al., "RSD1000: A Novel Antiarrhythmic Agent with an Improved Therapeutic Index", BPS Proceedings 119P, 1996.

Yong et al., "SAR Evidence that Antiarrhythmic Activity is Unrelated to Opioid Kappa Agonist Activity", BPS Proceedings 117P, 1996.

Yong et al., "A Comparison of Four Chemically-Related $K^+$-Channel Blockers in Isolated Rat Ventricular Myocytes," Proceedings of the Western Pharmacology Society 43:121, 2000.

Zhang et al., "Inhibition of [3H]-U69593 binding and the cardiac effects of U50, 488H by calcium channel blockers in the rat heart", Brit J Pharmacol 120:827-832, 1997.

Zolotoy et al., "Physicochemical Determinants for Drug Induced Blockade of HERG Potassium Channels: Effect of Charge and Charge Shielding", Curr Med Chem 1(3): 1-17, 2003.

* cited by examiner

*Median time to conversion 11 minutes

*Symptoms reduced: shortness of breath, palpitation, chest tightness and pain, dizziness, rapid heart beat, irregular pulse, headache

DOSING REGIMENS FOR ION CHANNEL MODULATING COMPOUNDS

FIELD OF INVENTION

This invention is directed to dosing regimens for certain ion channel modulating compounds and methods of producing in the plasma of a human a certain concentration of an ion channel modulating compound for a period of time. The invention is also directed to methods of treating or preventing arrhythmia in a human, particularly the treatment or prevention of atrial fibrillation, atrial flutter, Torsades de Pointes, acquired long QT-Syndrome, multifocal ventricular arrhythmia, and supraventricular arrhythmia.

BACKGROUND

Cardiac arrhythmias often occur as complications to cardiac diseases such as myocardial infarction and heart failure. In serious cases, arrhythmias can cause sudden death. Treatment of arrhythmias is complex and aspects of care, especially the decision to control the ventricular rate vs. convert the arrhythmia, remain controversial.

Class III antiarrhythmics ($I_{Kr}$ blockers) are commonly used to treat arrhythmia; however these drugs have also been shown to be proarrhythmic and cause greater lengthening in Purkinje fiber action potentials relative to those in ventricular muscle, presumably due to a greater contribution of $I_{Kr}$ in repolarization of Purkinje fibers. For example, dofetilide (10 nM) has been shown to increase the APD90 (the action potential duration at 90% repolarization) of rabbit Purkinje fibers by 83%, (basic cycle lengths, or BCL=1000 ms). Similarly, quinidine (10 µM) increased APD90 by 93% in the rabbit. In addition to drug induced dispersion of repolarization, drug induced early after depolarizations (EADs) are thought to be an important cause of Torsades de Pointes (TdP) both clinically and in animal models.

Class III agents have been shown to be proarrhythmic due to blockade of the hERG potassium channel ($I_{Kr}$ current in human ventricle). hERG channels refer to the product of expression of the human ether-a-go-go related gene, normally considered to be a potassium-conducting ion channel. It has been shown that combination therapy with quinidine (class III agent) and mexiletine (class I agent and sodium channel blocker) is more effective in the prevention of ventricular tachycardia (VT) and ventricular fibrillation (VF) in animal models and in humans. In isolated hearts, these effects have been shown to be due to sodium channel blockade. EAD generation is thought to be a major cause of TdP in humans. In addition, EADs have been shown to contribute to reinduction of atrial fibrillation (AF) following termination in isolated coronary-perfused canine right atria. Sodium channel blockers have been shown to prevent isoproterenol-induced TdP in a canine model and also abbreviate action potential duration in M-cells of the ventricular myocardium.

High densities of voltage-gated sodium channels in excitable tissues lead to a rapid membrane depolarization when excitable cells reach the threshold for sodium channel activation. The role of sodium channels in the action potential upstroke (Phase 0) has been well-characterized and block of sodium channels can affect cellular refractoriness and regulate heart rhythms. Sodium channels rapidly inactivate following initial opening during Phase 0 and during repolarization. Recovery of these inactivated channels is critical in determining the ability of a cell to generate another action potential. The period during which the cell cannot generate another action potential is known as the effective refractory period (ERP). Blockade of sodium channels can lengthen the refractory period of the cell and this activity is known to have antiarrhythmic consequences due to prolongation of the effective wavelength of the tissue, reducing the size of reentrant wavelets which the tissue can support. Blockade of sodium channels can also suppress ectopic beats which may also play a role in the genesis of fibrillatory activity in the heart. Indeed, the selective sodium channel blocker tetrodotoxin (TTX) has been shown to prevent VF in isolated rabbit hearts. Recent evidence has shown that sodium channel activity contributes not only to the action potential upstroke, but also can affect the action potential plateau (Phase 2) and repolarization (Phase 3). This sustained activity is thought to be a result of 3 separate mechanisms. The first of such mechanisms has been described as channel bursting in which the channel fails to inactivate. A second component is known as window current and occurs at potentials at which the steady-state activation and inactivation curves overlap. The third mechanism is a non-equilibrium phenomenon in which the sodium channels recover from inactivation during the repolarization phase. The sustained inward sodium current contributed by these three mechanisms can modulate repolarization during Phase 2 and Phase 3 of the action potential when the membrane potential is regulated by small amounts of both inward and outward current. Modulation of currents contributing to Phase 0, 2 and 3 of the action potential can have important roles in regulating refractoriness, action potential duration and EAD generation.

The ion channel modulating compounds described herein are atrially-selective, and block sodium channels in a frequency (or stimulation) dependent manner. Further, these ion channel modulating compounds are capable of blocking the late, early and sustained components of a sodium channel current to prevent EADs without substantially interfering with cardiac activity.

The ion channel modulating compounds of the invention are described in PCT Published Patent Application, WO 99/50225; PCT Published Patent Application, WO 2004/099137; PCT Published Patent Application, WO 2004/098525; and PCT Published Patent Application, WO 2005/018635, the disclosures of which are incorporated in their entireties herein in full by reference.

SUMMARY OF THE INVENTION

Described herein are methods of using dosing regimens for the treatment, prevention, and/or termination of arrhythmias in a subject. In particular, described herein are methods of using dosing regimens for the treatment, prevention and/or termination of arrhythmia, including ventricular or atrial arrhythmia, particularly atrial fibrillation or atrial flutter, using certain ion channel modulating compounds. Also described herein are methods of producing in the plasma of a subject a concentration level of an ion channel modulating compound utilizing the dosing regimens described herein.

Accordingly, in one aspect, this invention is directed to a method of treating acute atrial fibrillation in a human, wherein the method comprises administering a therapeutic effective amount of an ion channel modulating compound in a pharmaceutically acceptable carrier to the human, wherein the ion channel modulating compound is a compound of formula (I):

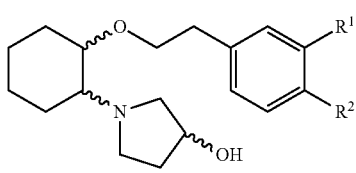

including isolated enantiomeric, diastereomeric and geometric isomers thereof and mixtures thereof, or a solvate or pharmaceutically acceptable salt thereof, wherein $R^1$ and $R^2$ are independently selected from hydrogen, hydroxy and $C_1$-$C_6$alkoxy; and wherein the compound of formula (I) is administered in accordance with a dosage regimen comprising the following sequential steps:
  a) administering over a first period of time a first dosage amount of between about 3.0 mg/kg and about 5.0 mg/kg of the compound of formula (I) to the human;
  b) determining after a second period of time if the acute atrial fibrillation has terminated in the human;
  c) if the acute atrial fibrillation has not terminated in the human after the second period of time, administering over a third period of time a second dosage amount of between about 0.5 mg/kg and about 2.0 mg/kg of the compound of formula (I) to the human; and
  d) optionally repeating step b) and c) until the acute atrial fibrillation has terminated.

In another aspect, this invention is directed to a method of treating acute atrial fibrillation in a human, wherein the method comprises administering a therapeutic effective amount of an ion channel modulating compound in a pharmaceutically acceptable carrier to the human, wherein the ion channel modulating compound is a compound of formula (I):

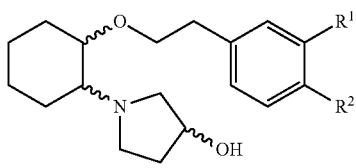

including isolated enantiomeric, diastereomeric and geometric isomers thereof and mixtures thereof, or a solvate or pharmaceutically acceptable salt thereof, wherein $R^1$ and $R^2$ are independently selected from hydrogen, hydroxy and $C_1$-$C_6$alkoxy; and wherein the compound of formula (I) is administered in accordance with a dosage regimen comprising the following sequential steps:
  a) administering over a first period of time a first dosage amount of between about 3.0 mg/kg and about 5.0 mg/kg of the compound of formula (I) to the human;
  b) administering over a second period of time a second dosage amount of between about 0.5 mg/kg and about 2.0 mg/kg or between about 1.0 mg/kg/hr and about 2.0 mg/kg/hr of the compound of formula (I) to the human; and
  c) optionally repeating step b) and c) until the acute atrial fibrillation has terminated.

In another aspect, this invention is directed to the use of an ion channel modulating compound for the preparation of a medicament for the treatment of acute atrial fibrillation in a human, wherein the ion channel modulating compound is a compound of formula (I):

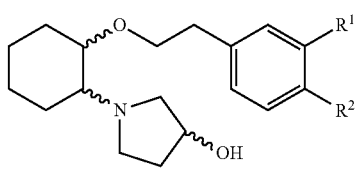

including isolated enantiomeric, diastereomeric and geometric isomers thereof and mixtures thereof, or a solvate or pharmaceutically acceptable salt thereof, wherein $R^1$ and $R^2$ are independently selected from hydrogen, hydroxy and $C_1$-$C_6$alkoxy; and wherein the medicament is formulated to be administered to the human in accordance with a dosage regimen comprising the following sequential steps:
  a) administering over a first period of time a first dosage amount of between about 3.0 mg/kg and about 5.0 mg/kg of the medicament;
  b) determining after a second period of time if the acute atrial fibrillation has terminated in the human;
  c) if the acute atrial fibrillation has not terminated in the human after the second period of time, administering over a third period of time a second dosage amount of between about 0.5 mg/kg and about 2.0 mg/kg of the medicament; and
  d) optionally repeating step b) and c) until the acute atrial fibrillation has terminated.

In another aspect, this invention is directed to the use of an ion channel modulating compound for the preparation of a medicament for the treatment of acute atrial fibrillation in a human, wherein the ion channel modulating compound is a compound of formula (I):

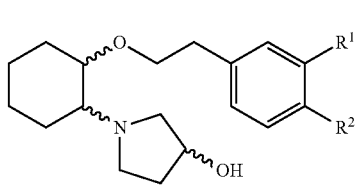

including isolated enantiomeric, diastereomeric and geometric isomers thereof and mixtures thereof, or a solvate or pharmaceutically acceptable salt thereof, wherein $R^1$ and $R^2$ are independently selected from hydrogen, hydroxy and $C_1$-$C_6$alkoxy; and wherein the medicament is formulated to be administered in accordance with a dosage regimen comprising the following sequential steps:
  a) administering over a first period of time a first dosage amount of between about 3.0 mg/kg and about 5.0 mg/kg of the medicament to the human;
  b) administering over a second period of time a second dosage amount of between about 0.5 mg/kg and about 2.0 mg/kg or between about 1.0 mg/kg/hr and about 2.0 mg/kg/hr of the medicament to the human; and
  c) optionally repeating step b) and c) until the acute atrial fibrillation has terminated.

The various and specific dosing regimens of the invention are described in detail in the Detailed Description section below. In one version of the dosing regimens, the dosing regimen is administered to the subject intravenously. In another version of the dosing regimens, the dosing regimen is adminstered to the subject orally. The oral and intravenous formulations utilized by the dosing regimens may include one or more ion channel modulating compounds together with other optional components. The oral and intravenous formulations may or may not be administered via the same route of administration during a particular dosing regimen. The formulations may also be delivered by repeat dosing and by substantially continuous dosing;

In one version of the invention, the ion channel modulating compound utilized in the dosing regimens of the invention is a compound that blocks an early component of a cardiac sodium channel current; wherein the ion channel modulating compound further blocks the early component of a cardiac sodium channel current approximately as much as or more than it blocks a sustained component of a cardiac sodium channel current. In some versions, the ion channel modulating compound blocks a late component of a cardiac sodium channel approximately 20% more than it blocks the early component of a cardiac sodium channel current.

In another version of the invention, the ion channel modulating compound used in the dosing regimens of the invention is a hydrochloride salt of the compound of formula (Ib):

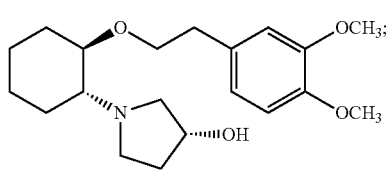

(Ib)

including isolated enantiomeric, diastereomeric and geometric isomers thereof and mixtures thereof.

For all ion channel modulating compounds described above and elsewhere herein, isolated enantiomeric, diastereomeric and geometric isomers of the compounds may be used and mixtures of the compounds may be used in the dosing regimens of the invention. In addition, solvates or pharmaceutically acceptable salts of the compounds may be used in the dosing regimens of the invention.

DETAILED DESCRIPTION OF THE INVENTION

Definitions

Figure 1:
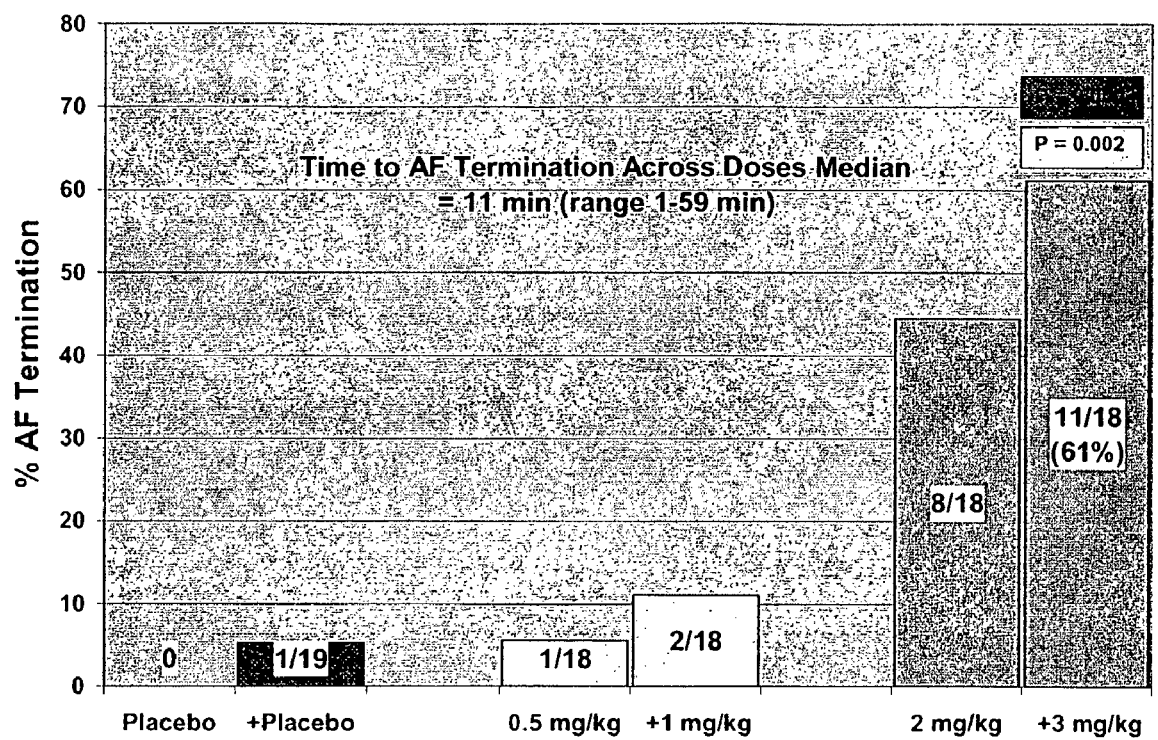
FIG. 1 shows the cumulative percentage of patients terminating atrial fibrillation (AF) after infusions of placebo, 0.5 and 1 mg/kg COMPOUND A or 2.0 and 3.0 mg/kg COMPOUND A, in patients with recent onset AF (3 h-72 h duration).

As used herein, a "subject" may generally be any human or non-human animal that would benefit from the methods described in this application. In one version of the methods, a subject is a human. In some versions of the methods, a subject is a mammal. In some versions, the subject is any domestic animal, including, but not limited to dogs, and cats. In some versions, the subject is any livestock animal, including but not limited to horses, pigs, and cattle. In some versions, the subject is any zoo animal, including but not limited to Bengal tigers.

As used herein, unless the context makes clear otherwise, "treatment," and similar word such as "treated," "treating" etc., is an approach for obtaining beneficial or desired results, including and preferably clinical results. Treatment can involve optionally either the amelioration of symptoms of the disease or condition, or the delaying of the progression of the disease or condition.

As used herein, unless the context makes clear otherwise, "prevention," and similar word such as "prevented," "preventing" etc., is an approach for preventing the onset of a disease or condition or preventing the occurrence of the symptoms of a disease or condition, or optionally an approach for delaying the onset of a disease or condition or delaying the occurrence of the symptoms of a disease or condition. As used herein, "prevention" and similar words also includes reducing the intensity, effect, symptoms and/or burden of a disease or condition prior to onset of the disease or condition.

As used herein, an "effective amount" or a "therapeutically effective amount" of a substance is that amount sufficient to affect a desired biological effect, such as beneficial results, including clinical results.

As used herein, unless the context makes clear otherwise, "inhibition" and similar words such as "inhibit" of any ion channel means any decrease in current through that channel. When "inhibition" is used in the context of a specified concentration, it is determined by the $IC_{50}$. For example, an ion channel modulating compound which inhibits an ion channel at a concentration of 1 µM, the ion channel may be said to have an $IC_{50}$ of 1 µM for that ion channel modulating compound. This example is for illustrative purposes only and is in no way intended to be limiting.

As used herein, unless the context makes clear otherwise, "$IC_{50}$" or "$IC_{50}$ concentration" means a drug concentration at which the specified current amplitude (peak or steady-state, or integrated current) is inhibited by 50%.

As used herein, unless the context makes clear otherwise, "blocking" or "block" of an ion channel means any block or inhibition of current through that ion channel.

As used herein, "rate-independent and use-independent" inhibition means inhibition that is predominantly heart rate and/or stimulus rate and use-independent such that there is no statistically significant effect of steady-state or transient changes in heart rate or stimulus rate with respect to the inhibition. For example, an ion channel modulating compound that inhibits Kv1 channels in a "rate-independent and use-independent" manner means that there is no influence of the heart rate or stimulus rate on the amount of inhibition produced by the ion channel modulating compound on Kv1 channels.

As used herein, "affects atrial repolarizing currents" means "has a statistically significant effect on atrial repolarizing current amplitudes."

As used herein, "prolongs atrial refractoriness" means "has a statistically significant prolonging effect on atrial refractoriness."

As used herein, "has substantially no effect on ventricular tissue" means "has no statistically significant effect on normal human ventricular action potential duration or refractoriness." Any apparent difference in effect, therefore, is attributed to intrinsic variability, such as in one aspect, less than a 10% difference.

As used herein, "does not substantially slow conduction" means "has no statistically significant effect on slowing conduction in the ventricles." As such, any apparent difference in effect, therefore, is attributed to intrinsic variability. In one aspect, the ion channel modulating compound has no statistically significant effect on the slowing of conduction wherein the compound produces less than a 15%, preferably less than a 10%, increase in cardiac QRS duration at physiological heart rates.

As used herein, "rate-dependent inhibition" of an ion channel means that the level of inhibition of the ion channel changes with the frequency of stimulation.

The terms 'early component,' 'late component' and 'sustained component' are used as known in the art; for example, the early, sustained and late components of a cardiac sodium channel current.

The term "QT interval" is used as is known in the art; for example, the QT interval as measured from an electrocardiogram. As used herein, unless the context makes clear otherwise, the term "prolongs" or "prolong" generally means extends or lengthens as in duration.

The term "antiarrhythmic" is used as is known in the art; for example, as a compound which prevents or alleviates irregularities in heart rate.

The term "induces" as used herein, unless the context indicates otherwise, generally means to stimulate the occurrence of.

As used herein, unless the context makes clear otherwise, the term "terminating" or "terminates" generally means to bring to an end or to halt.

The term "alkoxy" refers to an O-atom substituted by an alkyl group, for example, methoxy [—$OCH_3$, a $C_1$alkoxy].

The term "pharmaceutically acceptable salt" refers to salts of the compounds derived from the combination of such compounds and an organic or inorganic acid (acid addition salts) or an organic or inorganic base (base addition salts). "Acid addition salts" refer to those salts which retain the biological effectiveness and properties of the free bases and which are not biologically or otherwise undesirable, formed with inorganic acids such as hydrochloric acid, hydrobromic acid, sulfuric acid, nitric acid, phosphoric acid and the like, or organic acids such as acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid and the like. The compounds described herein may be used in either the free base or salt forms, with both forms being considered as being within the scope intended herein.

Often crystallizations produce a solvate of the compound of the invention. As used herein, the term "solvate" refers to an aggregate that comprises one or more molecules of a compound of the invention with one or more molecules of solvent. The solvent may be water, in which case the solvate may be a hydrate. Alternatively, the solvent may be an organic solvent. Thus, the compounds of the present invention may exist as a hydrate, including a monohydrate, dihydrate, hemihydrate, sesquihydrate, trihydrate, tetrahydrate and the like, as well as the corresponding solvated forms. The compound of the invention may be true solvates, while in other cases, the compound of the invention may merely retain adventitious water or be a mixture of water plus some adventitious solvent.

The term "modulating" in connection with the activity of an ion channel means that the activity of the ion channel may be either increased or decreased in response to administration of a compound or composition or method described herein. Thus, the ion channel may be activated, so as to transport more ions, or may be blocked, so that fewer or no ions are transported by the channel.

The term "pharmaceutically acceptable carriers" for therapeutic use are well known in the pharmaceutical art, and are described, for example, in *Remingtons Pharmaceutical Sciences*, Mack Publishing Co. (A. R. Gennaro edit. 1985). For example, sterile saline and phosphate-buffered saline at physiological pH may be used. Preservatives, stabilizers, dyes and even flavoring agents may be provided in the pharmaceutical composition. For example, sodium benzoate, sorbic acid and esters of p-hydroxybenzoic acid may be added as preservatives. Id. at 1449. In addition, antioxidants and suspending agents may be used. Id.

As used herein, "mg/kg" means the amount of ion channel modulating compound or compounds per kg body weight of the subject. For example, but without limitation, to administer 0.1 mg/kg of ion channel modulating compound to a subject of mass 50 kg the administered dose contains 5 mg of ion channel modulating compound or compounds.

Following the standard chemical literature description practice and as used herein for the formulae of the ion channel modulating compounds of the invention, a wavy bond from a substituent to the central cyclohexane ring of a compound indicates that the substituent may be located on either side of the plane of the central cyclohexane ring; a full wedge bond means that the substituent is above the ring plane; and a dashed wedge bond means that the substituent is below the ring plane. In addition; one full bond and one dashed bond (i.e., ⎯⎯⎯⎯⎯) for the bonds from the cyclohexane ring to the substituent at the 1 position of the cyclohexane ring and the substituent at the 2 position of the cyclohexane ring means that the substituents are in a trans relationship with respect to each other and the plane of the cyclohexane ring, whereas two full bonds or two dashed bonds means that the substituents are in a cis relationship with respect to each other and the plane of the cyclohexane ring.

General Description of Ion Channel Modulating Compounds

For purposes of this invention, any compound that either singly or together with one or more additional compounds selectively inhibit certain combination of cardiac ionic currents is an ion channel modulating compound. The cardiac currents may be the sodium currents and early repolarizing currents. Ion channel modulating compounds of the invention may block cardiac currents from any loci. Such compounds may block the ion channel with rapid onset and offset kinetics and exhibits frequency dependent blockade of currents. Such properties are all beneficial for compounds used to treat arrhythmias.

An ion channel modulating compound of the invention may selectively inhibit cardiac early repolarizing currents and cardiac sodium currents. Ion channel modulating compounds of the invention may be used to selectively inhibit cardiac early repolarizing currents and cardiac sodium currents under conditions where an "arrhythmogenic substrate" is present in the heart. An "arrhythmogenic substrate" is characterized by a reduction in cardiac action potential duration and/or changes in action potential morphology, premature action potentials, high heart rates and may also include increased variability in the time between action potentials and an increase in cardiac milieu acidity due to ischaemia or inflammation. Changes such as these are observed during conditions of myocardial ischaemia or inflammation and those conditions that precede the onset of arrhythmias such as atrial fibrillation or atrial flutter. An ion channel modulating compound of the invention may be an atrial selective agent. An ion channel modulating compound of the invention may treat or prevent ventricular arrhythmia. An ion channel modulating compounds of the invention may block cardiac sodium currents or cardiac early repolarizing currents. An ion channel modulating compound of the invention may inhibit multiple cardiac ionic currents. An ion channel modulating compound of the invention may be used to treat or prevent arrhythmia, including ventricular or atrial arrhythmia, particularly atrial fibrillation or atrial flutter.

The ion channel modulating compounds may block the cardiac ion channels responsible for early repolarizing currents and sodium currents; and/or block cardiac early repolarizing currents and cardiac sodium currents under conditions where an arrhythmogenic substrate is present in the heart; and/or block the cardiac ion channels responsible for early repolarizing currents and sodium currents under conditions where an arrhythmogenic substrate is present in the heart; and/or block cardiac early repolarizing currents and cardiac sodium currents from extracellular, intracellular loci or within the plasma membrane in cardiac cells.

In one variation, the cardiac early repolarizing currents referred to above comprise ionic currents which activate rapidly after depolarization of membrane voltage and which effect repolarization of the cell. The early repolarizing currents may comprise the cardiac transient outward potassium current ($I_{to}$) and/or the ultrarapid delay rectifier current ($I_{Kur}$). The cardiac transient outward potassium current ($I_{to}$) and/or the ultrarapid delay rectifier current ($I_{Kur}$) may comprise at least one of the Kv4.2, Kv4.3, Kv2.1, Kv1.4 and Kv1.5 currents.

Ion channel modulating compounds may generally have any pKa, however ion channel modulating compounds typically have pKa values of between 4-9, and may have pKa values that are less than 8, including pKa values between 5-7.5. Methods to determine pKa values are well known in the art (see, e.g., Perrin, "Dissociation Constants of Organic Bases in Aqueous Solution", Butterworth, London, 1972).

Ion Channel Modulating Compounds of the Invention

Ion channel modulating compounds useful in the dosing regimens and methods of this invention are described in detail in PCT Published Patent Application, WO 99/50225; PCT Published Patent Application, WO 2004/099137; PCT Published Patent Application, WO 2004/098525; and PCT Published Patent Application, WO 2005/018635, the disclosures of which are incorporated in their entireties herein in full by reference.

All racemic, enantiomeric and diastereomeric forms, and mixtures thereof, of the ion channel modulating compounds are intended for use in this invention. Pure stereoisomers, mixtures of enantiomers and/or diastereomers, and mixtures of different ion channel modulating compounds are described in the afore-mentioned patent applications. Thus, the ion channel modulating compounds useful in the invention may occur as racemates, racemic mixtures and as individual diastereomers or enantiomers with all isomeric forms being included in the present description. For the present invention, a racemate or racemic mixture does not imply a 50:50 mixture of stereoisomers only. Other enantiomerically enriched mixtures of varying ratios of stereoisomers are also contemplated. Where a given structural formula or chemical name is presented for a compound it is intended that all possible solvates, pharmaceutically acceptable salts, esters, amides, complexes, chelates, stereoisomers, geometric isomers, crystalline or amorphous forms, metabolites, metabolic precursors or prodrugs of the compound are also separately described by the chemical structural formula or chemical name.

In one version of the invention, the ion channel modulating compounds used in the dosing regimens and methods of the invention are compounds of formula (I)

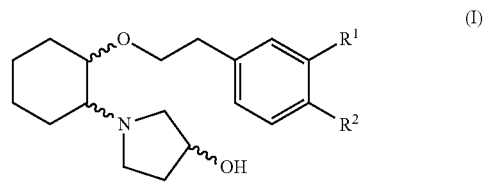

(I)

including isolated enantiomeric, diastereomeric and geometric isomers thereof and mixtures thereof, or a solvate or pharmaceutically acceptable salt thereof, wherein $R^1$ and $R^2$ are independently selected from hydrogen, hydroxy and $C_1$-$C_6$alkoxy.

In another version of the invention, the ion channel modulating compound used in the dosing regimens and methods of the invention is a compound of formula (I), as described above, wherein $R^1$ and $R^2$ are both methoxy.

In another version of the invention, the ion channel modulating compound used in the dosing regimens and methods of the invention is a compound of formula (Ia):

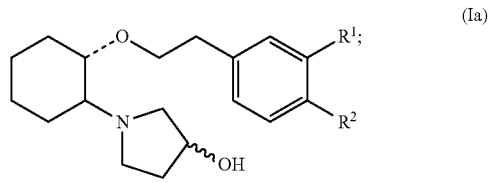

(Ia)

including isolated enantiomeric, diastereomeric and geometric isomers thereof and mixtures thereof, or a solvate or pharmaceutically acceptable salt thereof, wherein $R^1$ and $R^2$ are independently selected from hydrogen, hydroxy and $C_1$-$C_6$alkoxy, and wherein the In another version of the invention, the ion channel modulating compound used in the dosing regimens and methods of the invention is a compound of formula (Ia), as described above, wherein $R^1$ and $R^2$ are both methoxy.

In another version of the invention, the ion channel modulating compound used in the dosing regimens and methods of the invention is a compound of formula (Ib):

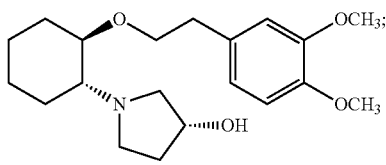

or a solvate or pharmaceutically acceptable salt thereof. The compound of formula (Ib) is named herein as (1R,2R)-2-[(3R)-hydroxypyrrolidinyl]-1-(3,4-dimethoxyphenethoxy)cyclohexane.

In another version of the invention, the compound of formula (I) is the hydrochloride salt of the compound of formula (Ib). This hydrochloride salt of the compound of formula (Ib) is identified herein as COMPOUND A and is named herein as (1R,2R)-2-[(3R)-hydroxypyrrolidinyl]-1-(3,4-dimethoxyphenethoxy)cyclohexane monohydrochloride.

In one variation, the ion channel modulating compound used in the dosing regimens and methods of the invention contains a cyclohexyl ring, wherein the cyclohexyl ring comprises two adjacent substituents, such as substituents at the 1 and 2 position of the cyclohexyl ring, wherein the two adjacent substituents are situated in a trans position relative to one another. In another variation, the two adjacent substituents are situated in a cis position relative to one another.

In another version of the invention, the ion channel modulating compound used in the dosing regimens and methods of the invention is a compound or any pharmaceutically acceptable salt thereof, or any solvate thereof, or mixture comprising one or more said compounds or any pharmaceutically acceptable salt thereof, or any solvate thereof, of the formula (Ia):

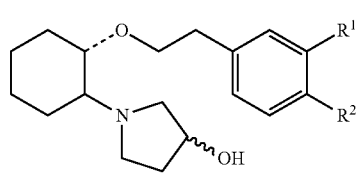

and is selected from the group consisting of (1R,2R)-2-(3-hydroxypyrrolidinyl)-1-(3,4-dimethoxyphenethoxy)cyclohexane monohydrochloride or (1S,2S)-2-(3-hydroxypyrrolidinyl)-1-(3,4-dimethoxyphenethoxy)cyclohexane monohydrochloride or a mixture of (1R,2R)-2-(3-hydroxypyrrolidinyl)-1-(3,4-dimethoxyphenethoxy)cyclohexane monohydrochloride and (1S,2S)-2-(3-hydroxypyrrolidinyl)-1-(3,4-dimethoxyphenethoxy)cyclohexane monohydrochloride, wherein the hydroxyl moiety in any of the above may be in the R or S stereochemical configuration.

In another version of the invention, the ion channel modulating compound used in the dosing regimens and methods of the invention is a compound or a mixture comprising compounds, or any solvate thereof, selected from the group consisting of:

| Structure | Chemical name |
|---|---|
| 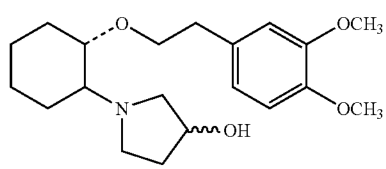 | (1R,2R)-2-[(3R)/(3S)-Hydroxypyrrolidinyl]-1-(3,4-dimethoxyphenethoxy)cyclohexane or (1S,2S)-2-[(3R)/(3S)-hydroxypyrrolidinyl]-1-(3,4-dimethoxyphen ethoxy)cyclohexane or a mixture of (1R,2R)-2-[(3R)/(3S)-hydroxypyrrolidinyl]-1-(3,4-dimethoxyphenethoxy)cyclohexane and (1S,2S)-2-[(3R)/(3S)-hydroxypyrrolidinyl]-1-(3,4-dimethoxyphenethoxy)cyclohexane, where the designation (3R)/(3S) indicates the stereochemistry at the 3-position may be R or S. |
| 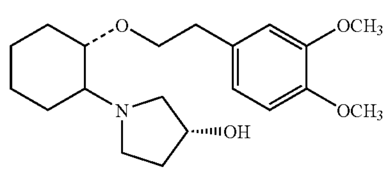 | (1R,2R)-2-[(3R)-Hydroxypyrrolidinyl]-1-(3,4-dimethoxyphenethoxy)cyclohexane or (1S,2S)-2-[(3R)-hydroxypyrrolidinyl]-1-(3,4-dimethoxyphenethoxy)cyclohexane and a mixture of (1R,2R)-2-[(3R)-hydroxypyrrolidinyl]-1-(3,4-dimethoxyphenethoxy)cyclohexane and (1S,2S)-2-[(3R)-hydroxypyrrolidinyl]-1-(3,4-dimethoxyphenethoxy)cyclohexane |
| 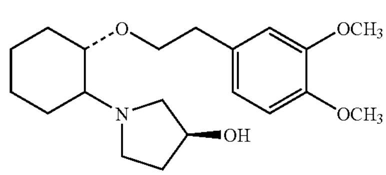 | (1R,2R)-2-[(3S)-Hydroxypyrrolidinyl]-1-(3,4-dimethoxyphenethoxy)cyclohexane or (1S,2S)-2-[(3S)-hydroxypyrrolidinyl]-1-(3,4-dimethoxyphenethoxy)cyclohexane and a mixture of (1R,2R)-2-[(3S)-hydroxypyrrolidinyl]-1-(3,4-dimethoxyphenethoxy)cyclohexane and (1S,2S)-2-[(3S)-hydroxypyrrolidinyl]-1-(3,4-dimethoxyphenethoxy)cyclohexane |
| 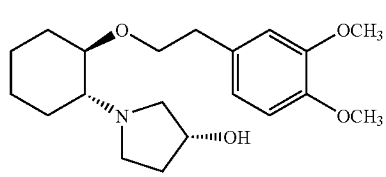 | (1R,2R)-2-[(3R)-Hydroxypyrrolidinyl]-1-(3,4-dimethoxyphenethoxy)cyclohexane |

-continued

| Structure | Chemical name |
|---|---|
| 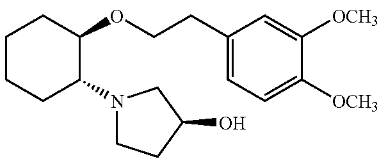 | (1R,2R)-2-[(3S)-Hydroxypyrrolidinyl]-1-(3,4-dimethoxyphenethoxy)cyclohexane |
| 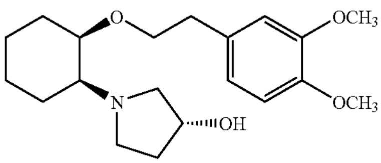 | (1R,2S)-2-[(3R)-Hydroxypyrrolidinyl]-1-(3,4-dimethoxyphenethoxy)cyclohexane |
| 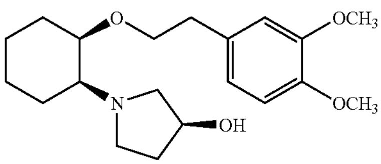 | (1R,2S)-2-[(3S)-Hydroxypyrrolidinyl]-1-(3,4-dimethoxyphenethoxy)cyclohexane |
| 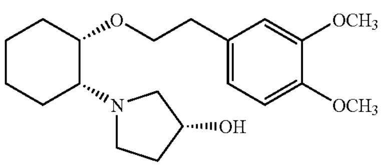 | (1S,2R)-2-[(3R)-Hydroxypyrrolidinyl]-1-(3,4-dimethoxyphenethoxy)cyclohexane |
| 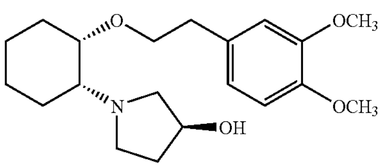 | (1S,2R)-2-[(3S)-Hydroxypyrrolidinyl]-1-(3,4-dimethoxyphenethoxy)cyclohexane |
| 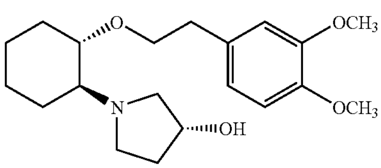 | (1S,2S)-2-[(3R)-Hydroxypyrrolidinyl]-1-(3,4-dimethoxyphenethoxy)cyclohexane |
| 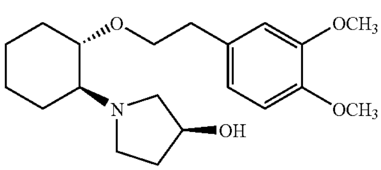 | (1S,2S)-2-[(3S)-Hydroxypyrrolidinyl]-1-(3,4-dimethoxyphenethoxy)cyclohexane |
| 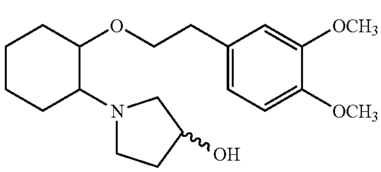 | (1R,2S)-2-[(3R)/(3S)-Hydroxypyrrolidinyl]-1-(3,4-dimethoxyphenethoxy)cyclohexane or (1S,2R)-2-[(3R)/(3S)-hydroxypyrrolidinyl]-1-(3,4-dimethoxyphen ethoxy)cyclohexane or a mixture of (1R,2S)-2-[(3R)/(3S)-hydroxypyrrolidinyl]-1-(3,4-dimethoxyphenethoxy)cyclohexane and (1S,2R)-2-[(3R)/(3S)-hydroxypyrrolidinyl]-1-(3,4-dimethoxyphen ethoxy)cyclohexane, where the designation (3R)/(3S) indicates the stereochemistry at the 3-position may be R or S. |
| 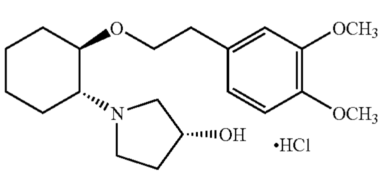 | (1R,2R)-2-[(3R)-Hydroxypyrrolidinyl]-1-(3,4-dimethoxyphenethoxy)cyclohexane monohydrochloride |

| Structure | Chemical name |
|---|---|
| 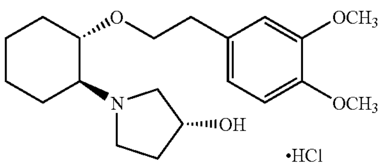 | (1S,2S)-2-[(3R)-Hydroxypyrrolidinyl]-1-(3,4-dimethoxyphenethoxy)cyclohexane monohydrochloride |
| 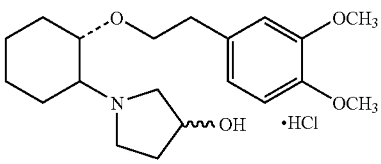 | (1R,2R)-2-[(3R)/(3S)-Hydroxypyrrolidinyl]-1-(3,4-dimethoxyphenethoxy)cyclohexane monohydrochloride or (1S,2S)-2-[(3R)/(3S)-hydroxypyrrolidinyl]-1-(3,4-dimethoxyphenethoxy)cyclohexane monohydrochloride or a mixture of (1R,2R)-2-[(3R)/(3S)-hydroxypyrrolidinyl]-1-(3,4-dimethoxyphenethoxy)cyclohexane monohydrochloride and (1S,2S)-2-[(3R)/(3S)-hydroxypyrrolidinyl]-1-(3,4-dimethoxyphenethoxy)cyclohexane monohydrochloride, where the designation (3R)/(3S) indicates the stereochemistry at the 3-position may be R or S. |
| 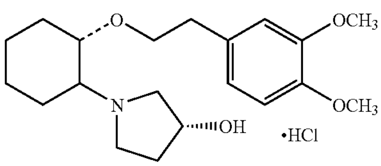 | (1R,2R)-2-[(3R)-Hydroxypyrrolidinyl]-1-(3,4-dimethoxyphenethoxy)cyclohexane monohydrochloride or (1S,2S)-2-[(3R)-hydroxypyrrolidinyl]-1-(3,4-dimethoxyphenethoxy)cyclohexane monohydrochloride or a mixture of (1R,2R)-2-[(3R)-hydroxypyrrolidinyl]-1-(3,4-dimethoxyphenethoxy)cyclohexane monohydrochloride and (1S,2S)-2-[(3R)-hydroxypyrrolidinyl]-1-(3,4-dimethoxyphenethoxy)cyclohexane monohydrochloride |
| 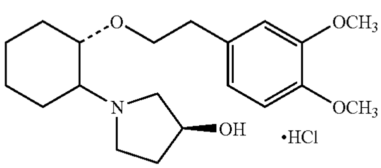 | (1R,2R)-2-[(3S)-Hydroxypyrrolidinyl]-1-(3,4-dimethoxyphenethoxy)-cyclohexane monohydrochloride or (1S,2S)-2-[(3S)-hydroxypyrrolidinyl]-1-(3,4-dimethoxyphenethoxy)cyclohexane monohydrochloride or a mixture of (1R,2R)-2-[(3S)-hydroxypyrrolidinyl]-1-(3,4-dimethoxyphenethoxy)cyclohexane monohydrochloride and (1S,2S)-2-[(3S)-hydroxypyrrolidinyl]-1-(3,4-dimethoxyphenethoxy)cyclohexane monohydrochloride |
| 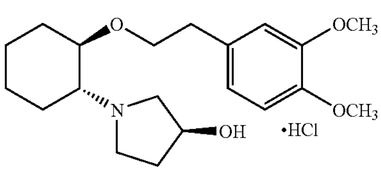 | (1R,2R)-2-[(3S)-Hydroxypyrrolidinyl]-1-(3,4-dimethoxyphenethoxy)cyclohexane monohydrochloride |
| 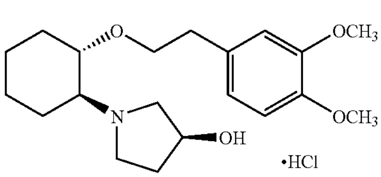 | (1S,2S)-2-[(3S)-Hydroxypyrrolidinyl]-1-(3,4-dimethoxyphenethoxy)cyclohexane monohydrochloride |

In another version of the invention, the ion channel modulating compound used in the dosing regimens and methods of the invention is one of the following compounds: (1R,2R)-2-[(3R)-hydroxypyrrolidinyl]-1-(3,4-dimethoxyphenethoxy) cyclohexane free base or any salt thereof, or any solvate thereof; (1R,2R)-2-[(3S)hydroxypyrrolidinyl]-1-(3,4-dimethoxyphenethoxy)-cyclohexane free base or any salt thereof, or any solvate thereof; (1S,2S)-2-[(3R)-hydroxypyrrolidinyl]-1-(3,4-dimethoxyphenethoxy)-cyclohexane free base or any salt thereof, or any solvate thereof; (1S,2S)-2-[(3S)-hydroxypyrrolidinyl]-1-(3,4-dimethoxyphenethoxy) cyclohexane free base or any salt thereof, or any solvate thereof; (1R,2R)-2-[(3R)-hydroxypyrrolidinyl]-1-(3,4-dimethoxyphenethoxy)-cyclohexane monohydrochloride, or any solvate thereof; (1R,2R)-2-[(3S)-hydroxypyrrolidinyl]-1-(3,4-dimethoxyphenethoxy)-cyclohexane monohydrochloride, or any solvate thereof; (1S,2S)-2-[(3R)-hydroxypyrrolidinyl]-1-(3,4-dimethoxyphenethoxy)-cyclohexane monohydrochloride, or any solvate thereof; or (1S,2S)-2-[(3S)-hydroxypyrrolidinyl]-1-(3,4-dimethoxyphenethoxy)-cyclohexane monohydrochloride, or any solvate thereof.

In another version of the invention, the ion channel modulating compound used in the dosing regimens and methods of the invention is a protonated version of any of the aminocyclohexyl ether compounds described herein. That is, for each ion channel modulating compound described herein, the quaternary protonated amine form of the compound may also be considered as an ion channel modulating compound. These quaternary protonated amine forms of the compounds may be present in the solid phase, for example in crystalline or amorphous form, and may be present in solution. These quaternary protonated amine forms of the compounds may be associated with pharmaceutically acceptable anionic counter ions, including but not limited to those described in for example: "Handbook of Pharmaceutical Salts, Properties, Selection, and Use", P. Heinrich Stahl and Camille G. Wermuth (Eds.), Published by VHCA (Switzerland) and Wiley-VCH (FRG), 2002.

Methods of Making Ion Channel Modulating Compounds

Methods that may be used to synthesize the ion channel modulating compounds for use in the dosing regimens and methods described herein include, but are not limited to, the synthesis methods described in PCT Published Patent Application, WO 99/50225; PCT Published Patent Application, WO 2004/099137; PCT Published Patent Application, WO 2004/098525; and PCT Published Patent Application, WO 2005/018635, the disclosures of which are incorporated in their entireties herein in full by reference.

Dosage Forms, Routes of Administration, and Formulations of Ion Channel Modulating Compounds Dosage forms, routes of administration, and formulations of the ion channel modulating compounds include, but are not limited to, those described in PCT Published Patent Application, WO 99/50225; PCT Published Patent Application, WO 2004/099137; PCT Published Patent Application, WO 2004/098525; and PCT Published Patent Application, WO 2005/018635, the disclosures of which are incorporated in their entireties herein in full by reference. Any effective dosage forms, routes of administration, and formulations may generally be used with any and all other aspects described herein.

The ion channel modulating compounds and formulations described herein may be formulated in a dosage form suitable for delivery via a variety of administration routes, including but not limited to oral, parenteral, mucosal, nasal, sublingual, transdermal, buccal, topical, vaginal, rectal, ocular or other administration. An ion channel modulating compounds as described herein may be in the form of an immediate and/or modified release formulation or it may be designed to release the ion channel modulating compound in a relatively fast manner in order to enable a relatively fast onset of the therapeutic effect. As used herein "compounds" and "compositions" of ion channel modulating compounds includes the ion channel modulating compounds as described herein alone or in combination with other materials.

Dosing Regimens of the Invention

Generally, the dosing regimen of the invention used for treatment of arrhythmia, particularly for the treatment of acute atrial fibrillation, will comprise the administration of at least one dosage amount of an ion channel modulating compound of the invention such that administration of the dosage amount of a therapeutically effective amount of the ion channel modulating compound will treat the arrhythmia in the subject.

The dosing regimen may comprise the administration of more than one dosage amounts. When administered as repeated dosage amounts, each individual dosage amount may or may not deliver a therapeutically effective amount of the ion channel modulating compound of the invention but the cumulative effect of the repeated dosage amounts will deliver a therapeutically effective amount of the ion channel modulating compound of the invention.

As set forth above in the Summary of the invention, one aspect of the invention is the use of a dosing regimen in a method to treat acute atrial fibrillation in a human, wherein the dosing regimen comprises the following sequential steps:

a) administering over a first period of time a first dosage amount of between about 3.0 mg/kg and about 5.0 mg/kg of the compound of formula (I), as described above in the Summary of the Invention, to the human;

b) determining after a second period of time if the acute atrial fibrillation has terminated in the human;

c) if the acute atrial fibrillation has not terminated in the human after the second period of time, administering over a third period of time a second dosage amount of between about 0.5 mg/kg and about 2.0 mg/kg of the compound of formula (I), as described above in the Summary of the Invention, to the human; and d) optionally repeating step b) and c) until the acute atrial fibrillation has terminated.

In a variation of this aspect, the dosage amount of the compound of formula (I) in step a) is about 3.0 mg/kg and the dosage amount of the compound in step b) is about 2.0 mg/kg.

In another variation of this aspect, the first period of time is between about 5 and about 15 minutes, the second period of time is between 0 and about 15 minutes, and the third period of time is between about 5 and about 15 minutes.

In another variation of this aspect, the first period of time is about 10 minutes, the second period of time is 15 minutes and the third period of time is about 10 minutes.

In another variation of this aspect, the first dosage amount and the second dosage amount are independently administered intravenously or orally.

In another variation of this aspect, the first dosage amount and the second dosage amount are both administered intravenously.

In another variation of this aspect, the first, second and any subsequent dosage amounts are all administered intravenously.

In another variation of this aspect, the compound of formula (I) is a compound of formula (Ia):

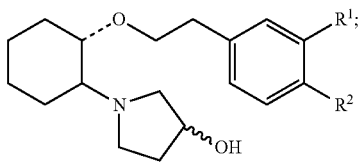

(Ia)

including isolated enantiomeric, diastereomeric and geometric isomers thereof and mixtures thereof, or a solvate or pharmaceutically acceptable salt thereof, wherein $R^1$ and $R^2$ are independently selected from hydrogen, hydroxy and $C_1$-$C_6$alkoxy.

In another variation of this aspect, the compound of formula (I) is a compound of formula (Ib):

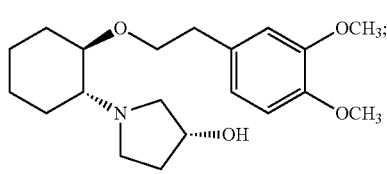

(Ib)

or a solvate or pharmaceutically acceptable salt thereof.

In another variation of this aspect, the compound of formula (I) is the hydrochloride salt of the compound of formula (Ib).

In another variation of this aspect, the ion channel modulating compound of formula (I) is the hydrochloride salt of the compound of formula (Ib), as described above, wherein the dosage regimen comprises the following sequential steps:

a) intravenously administering over a first period of time of about 10 minutes a first dosage amount of about 3.0 mg/kg of the hydrochloride salt of the compound of formula (Ib) to the human;

b) determining after a second period of time of about 15 minutes if the acute atrial fibrillation has terminated; and c) if the acute atrial fibrillation has not terminated in the human after the second period of time, administering over a third period of time of about 10 minutes a second dosage amount of about 2.0 mg/kg of the hydrochloride salt of the compound of formula (Ib) to the human.

As set forth above in the Summary of the invention, another aspect of the invention is the use of a dosing regimen in a method to treat acute atrial fibrillation in a human, wherein the dosing regimen comprises the following sequential steps:

a) administering over a first period of time a first dosage amount of between about 3.0 mg/kg and about 5.0 mg/kg of the compound of formula (I), as described above in the Summary of the Invention, to the human;

b) administering over a second period of time a second dosage amount of between about 0.5 mg/kg and about 2.0 mg/kg or between about 1.0 mg/kg/hr and about 2.0 mg/kg/hr of the compound of formula (I), as described above in the Summary of the Invention, to the human; and c) optionally repeating step b) and c) until the acute atrial fibrillation has terminated.

In a variation of this aspect, the dosage amount of the compound of formula (I) in step a) is about 4.0 mg/kg and the dosage amount of the compound in step b) is about 0.5 mg/kg. or about 1 mg/kg/hr.

In another variation of this aspect, the first period of time is between about 5 and about 15 minutes and the second period of time is between about 5 and about 40 minutes.

In another variation of this aspect, the first period of time is about 10 minutes and the second period of time is about 35 minutes.

In another variation of this aspect, the first dosage amount and the second dosage amount are independently administered intravenously or orally.

In another variation of this aspect, the first dosage amount and the second dosage amount are both administered intravenously.

In another variation of this aspect, the first, second and any subsequent dosage amounts are all administered intravenously.

In another variation of this aspect, the compound of formula (I) is a compound of formula (Ia):

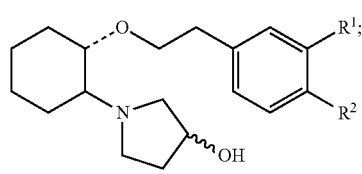

(Ia)

including isolated enantiomeric, diastereomeric and geometric isomers thereof and mixtures thereof, or a solvate or pharmaceutically acceptable salt thereof, wherein $R^1$ and $R^2$ are independently selected from hydrogen, hydroxy and $C_1$-$C_6$alkoxy.

In another variation of this aspect, the compound of formula (I) is a compound of formula (Ib):

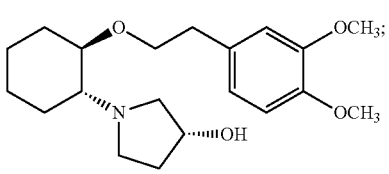

(Ib)

or a solvate or pharmaceutically acceptable salt thereof.

In another variation of this aspect, the compound of formula (I) is the hydrochloride salt of the compound of formula (Ib).

In another variation of this aspect, the compound of formula (I) is the hydrochloride salt of the compound of formula (Ib), as described above, wherein the hydrochloride salt of the compound of formula (Ib) is administered in accordance with a dosage regimen comprising the following sequential steps:

a) intravenously administering over a period of time of about 10 minutes a first dosage amount of about 4.0 mg/kg of the hydrochloride salt of the compound of formula (Ib) to the human;

b) intravenously administering over a period of time of about 35 minutes a second dosage amount of about 0.5 mg/kg. or about 1 mg/kg/hr of the hydrochloride salt of the compound of formula (Ib) the human.

In general, repeated dosage amounts do not have to be administered via the same route of administration. For example, a first dosage amount may be administered intravenously followed by a second dose administered orally. In addition, a therapeutically effective amount of the ion channel modulating compound or compounds may be delivered by administering more than one dosage amounts at the same time. As a nonlimiting example, a therapeutically effective amount of the ion channel modulating compound or compounds may be delivered by simultaneous or near simultaneous administration of dosage amounts both orally and intravenously.

Plasma Levels of Ion Channel Modulating Compounds in Methods of Treating Arrhythmias Generally the concentration of the ion channel modulating compound or compounds present in the subject's blood plasma after administration will be at a level sufficient to effect the required treatment of the subject's arrhythmia.

As used herein, unless the context makes it clear otherwise, the blood plasma level is the concentration of the ion channel modulating compound or compounds in the blood plasma of the subject after administration of a therapeutically effective amount of the ion channel modulating compound or compounds to the subject.

In one example in the treatment of a subject for acute atrial fibrillation by the administration of a therapeutically effective amount of an ion channel modulating compound of the invention to the subject, the dosing regimens of the invention produce in the blood plasma of the human a maximum concentration of greater than about 0.1 µg/ml of the ion channel modulating compound.

In one variation of this aspect of the invention, the maximum concentration is between about 0.3 µg/ml and about 20 µg/ml.

In another variation of this aspect of the invention, the maximum concentration is less than about 12 µg/ml.

In another variation of this aspect of the invention, the maximum concentration is about 4 µg/ml.

In another variation of this aspect of the invention, the maximum concentration is between about 9.0 µg/ml and about 11.0 µg/ml.

In another variation of this aspect of the invention, the maximum concentration is about 11.0 µg/ml after the administration of the first dosage amount.

In another variation of this aspect of the invention, the maximum concentration is about 9.0 µg/ml after the administration of the first and second dosage amount.

In one nonlimiting example, these blood plasma levels are maintained by administering two or more repeated dosage amounts as described herein.

Use of Ion Channel Modulating Compounds to Treat or Prevent Certain Diseases and Conditions Ion channel modulating compounds may be used to treat or prevent various diseases and conditions as described herein. The compounds, compositions, formulations, methods, medicaments, etc. described herein may be used in the treatment and/or prevention of a variety of diseases and conditions, including arrhythmias such as ventricular arrhythmias (e.g., ventricular tachycardia, ventricular fibrillation, premature ventricular contractions), supraventricular arrhythmias (e.g., supraventricular tachycardia, atrial fibrillation, atrial flutter, Wolff-Parkinson-White Syndrome, premature supraventricular contractions), and arrhythmias associated with Long QT Syndrome or sick sinus syndrome. Other diseases or conditions that may be treated and/or prevented include but are not limited to disease of the central nervous system (CNS disorders), Lou Gehrig's disease (Amyotrophic Lateral Sclerosis), Alzheimer, AIDS-related dementia, Multiple Sclerosis (MS), convulsion, seizures, epileptic spasms, depression, insomnia, anxiety, schizophrenia, Parkinson's disease, trigeminal pain, phantom limb pain, back pain, smoke cessation, respiratory disorders, cystic fibrosis, asthma, cough, inflammation and inflammatory disorders, irritable bowel disorders, irritable bowel syndrome Crohn's disease, prostatic hyperplasia, insect bites, psoriasis, arthritis, allergies, gastrointestinal disorders, urinary incontinence, cardiovascular disorders, arrhythmia, heart failure, hypotension, cerebral or myocardial ischemias, hypertension, long-QT syndrome, stroke, migraine, ophthalmic diseases, diabetes mellitus, myopathies, Becker's myotonia, myasthenia gravis, paramyotonia congenita, malignant hyperthermia, hyperkalemic periodic paralysis, Thomsen's myotonia, autoimmune disorders, graft rejection in organ transplantation or bone marrow transplantation, alopecia, diseases or dysfunctions of ion channels and receptors, diseases of voltage-gated ion channels, paralysis. This list is illustrative of the kinds of disorders which could be treated and/or prevented as described herein, and is not intended to be either limiting or exhaustive.

The compounds, compositions and methods described herein may be used as antitoxins, anti-venoms, antivirals, antibiotics, antiparasitics, antineoplastics, antinociceptives, sedatives, anesthetics, analgesics, painkillers, antipsychotics, local anaesthetics, topical anesthetics, antiangiogenics, cardioplegias, and cardioprotectants.

The Examples below illustrate the use of ion channel modulating compounds of the invention, particularly the use of Compound A, in treating arrhythmia, particularly acute atrial fibrillation, in humans.

Effect of Ion Channel Modulating Compounds on Certain Ion Channel Characteristics and Other Physiological Characteristics The effects of ion channel modulating compounds on certain ion channel characteristics and other physiological characteristics are described in PCT Published Patent Application, WO 99/50225; PCT Published Patent Application, WO 2004/099137; PCT Published Patent Application, WO 2004/098525; and PCT Published Patent Application, WO 2005/018635, the disclosures of which are incorporated in their entireties herein in full by reference.

EXAMPLES

Unless otherwise indicated, the following abbreviations used in the following Examples have the following standard definitions "bpm" refers to beats per minute.

"BP" refers to blood pressure.

"AERP" refers to atrial effective refractory period.

"VERP" refers to ventricular effective refractory period.

"WCL" refers to Wenckebach cycle length.

"AH" refers to atrial H is interval.

"RF" refers to radiofrequency.

"QT" refers to QT interval on an electrocardiogram (ms).

"HV" refers to H is ventricular interval.

"PR" refers to PR interval on an electrocardiogram (ms).

"PA" refers to PA interval measured from the onset of the P wave to the onset of the low right atrial electrocardiogram during H is bundle recording.

"MAP" refers to monophasic action potential.

COMPOUND A refers to the hydrochloride salt of the compound of formula (Ib), as described herein, i.e., the salt of the following formula:

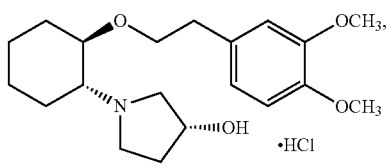

having a chemical name of (1R,2R)-2-[(3R)-hydroxypyrrolidinyl]-1-(3,4-dimethoxyphenethoxy)cyclohexane monohydrochloride, a molecular formula of $C_{20}H_{31}NO_4 \cdot HCl$, and a formula weight of 385.93 g/mol.

Example 1

An Example of the Electrophysiological Effects of Compound A on Human Cardiac Electrophysiology This example provides the results of a study conducted to determine the electrophysiological effects of two intravenous doses of COMPOUND A.

Inclusion Criteria for the Study:

Patients in the study required electrophysiologic studies (with or without radiofrequency ablation) and were from 18 to 75 years of age.

Exclusion Criteria for the Study:

Subjects having left ventricular ejection fraction of less than 45%; prior myocardial infarction; or coronary heart failure.

Subjects having more than 10 minutes of atrial fibrillation prior to or during the study.

Subjects having prolonged QT, sick sinus syndrome, or bradycardia.

Subjects taking any antiarrhythmic or cardioactive drug within 5 half-lives (such as beta blockers, calcium channel blockers, or digoxin).

Measurements of Electrophysiological Effects:

Following the study and ablation (if applicable), the atrial MAP catheter was positioned and the following electrophysiological measures were performed:

1. Intervals reflecting conduction: PA, AH, HV, QRS, at 600 msec A pacing
2. Intervals reflecting repolarization/refractoriness:
    a). Atrial MAP50 at CL 600, 400, 300, 250 and 200 msec
    b). AERP, VERP at 600, 400 msec & AERP at 300 ms
    c) Wenckebach Cycle Length
    d) QT interval with A and V pacing at 600, 400 msec
3. Sinus Node Recovery Time (SNRT) at 600, 400 msec.
4. Heart rate, brachial (cuff) blood pressure.

Drug Administration:

1. Dose Level 1 (n=10): 2 mg/kg in 10 min, then 0.5 mg/kg/hr for 35 minutes. Total dose was ~2.25 mg/kg
2. Dose level 2 (n=9): 4 mg/kg in 10 min, then 1.0 mg/kg/hr for 35 minutes. Total dose was ~4.5 mg/kg Blood samples for COMPOUND A concentrations were drawn at 0, 10 and 45 minutes after the start of drug infusion, and at discharge the next day.

Twenty five minutes after the start of intravenous drug infusion (15 minutes after the end of loading and start of maintenance infusion), all electrophysiological measures were repeated.

Subject Characteristics (n=19):

1. Mean age=48.4±10.9 years, 53% male
2. Indication for study with or without ablation:
    a) atrioventricular normal recovery time (AVNRT) (n=4)
    b) atrioventricular recovery time/Wolff Parkinson White (AVRT/WPW) (n=7
    c) atrial tachycardia (n=4)
    d) atrial flutter (n=3)
    e) Right ventricular outflow tract ventricular tachycardia (RVOT VT) (n=1)

Two patients exhibited mild structural abnormalities (1 patient with an enlarged RA, and 1 patient with mild cardiomyopathy).

Results:

The results of the study are shown below in Tables 4-17.

TABLE 1

Heart rate and blood pressure

|  | All (n = 19) Baseline | Dose Level 1 (n = 10) 2 mg/kg T = 45 min | Dose Level 2 (n = 9) 4 mg/kg T = 45 min |
|---|---|---|---|
| Heart Rate (bpm) | 81 ± 15 | 78 ± 11 | 91 ± 19 |
| Systolic BP (mm Hg) | 127 ± 15 | 135 ± 15 | 126 ± 15 |
| Diastolic BP (mm Hg) | 75 ± 12 | 84 ± 12 * | 75 ± 9 |
| Plasma Concentration of COMPOUND A (ng/mL) | BLQ ¥ (<5.0) | 1084.3 ± 279.1 | 2173.8 ± 422.0 |

* T = 45 min vs Baseline: paired ttest: p = 0.056; wilcoxon: p = 0.021
¥ BLQ = Below Limits of Quantification

TABLE 2

Intracardiac Conduction (600 msec pacing)

| | | Dose Level 1 | | Dose Level 2 | |
|---|---|---|---|---|---|
| Interval | Baseline (msec) | Ave Δ (msec) | Ave Δ (%) | Ave Δ (msec) | Ave Δ (%) |
| PA | 61.0 ± 17.3 | −4.1 ± 28.2 | 0.1 ± 38.5 | 15.9 ± 21.4 | 35.7 ± 54.0 |
| AH | 99.5 ± 24.0 | 10.6 ± 13.6 | 10.8 ± 13.3 | 3.7 ± 19.8 | 5.9 ± 21.9 |
| HV | 48.1 ± 10.6 | 0.1 ± 3.7 | 0.8 ± 7.1 | 6.4 ± 5.8 | 15.6 ± 13.3 |
| PR | 203.9 ± 35.2 | 15.0 ± 23.7 | 7.7 ± 12.9 | 27.3 ± 19.2 | 14.4 ± 11.5 * |

* Drug Infusion vs Baseline: p < 0.05 (wilcoxon)

All statistical comparisons were performed on paired values only. Baseline values shown are pooled (Dose Level 1 & 2 combined).

TABLE 3

Intracardiac Conduction (400 msec pacing)

| Interval | Baseline (msec) | Dose Level 1 Ave Δ (msec) | Dose Level 1 Ave Δ (%) | Dose Level 2 Ave Δ (msec) | Dose Level 2 Ave Δ (%) |
|---|---|---|---|---|---|
| PA | 63.3 ± 24.0 | −2.0 ± 13.5 | −4.2 ± 27.9 | 0.8 ± 22.5 | 5.8 ± 28.1 |
| AH | 122.5 ± 27.9 | 14.6 ± 51.3 | 10.0 ± 39.0 | 28.0 ± 48.3 | 18.3 ± 29.3 |
| HV | 45.4 ± 7.5 | −3.8 ± 3.9 | −7.6 ± 7.4 | 5.2 ± 5.3 | 12.8 ± 11.6 |
| PR | 238.6 ± 65.6 | 11.6 ± 33.6 | 3.7 ± 14.0 | 36.5 ± 44.2 | 16.2 ± 17.1 |

Drug Infusion vs Baseline: All comparisons NS

TABLE 4

Intracardiac Conduction (600 msec pacing)

| | Baseline | Dose Level 1 | Dose Level 2 |
|---|---|---|---|
| PA interval | 61.0 ± 17.3 | 64.0 ± 22.4 | 69.1 ± 21.5 |
| AH interval | 99.5 ± 24.0 | 113.8 ± 29.9 | 101.7 ± 21.5 |
| HV interval | 48.1 ± 10.6 | 50.1 ± 12.6 | 50.9 ± 7.0 |
| PR interval | 203.9 ± 35.2 | 227.7 ± 45.3 | 224.6 ± 18.8 * |

* Drug Infusion vs Baseline: p < 0.05 (wilcoxon)

TABLE 5

Intracardiac Conduction (400 msec pacing)

| | Baseline | Dose Level 1 | Dose Level 2 |
|---|---|---|---|
| PA interval | 63.3 ± 24.0 | 61.8 ± 30.2 | 75.8 ± 24.4 |
| AH interval | 122.5 ± 27.9 | 134.2 ± 69.2 | 147.0 ± 67.6 |
| HV interval | 45.4 ± 7.5 | 52.5 ± 13.6 | 50.2 ± 8.4 |
| PR interval | 238.6 ± 65.6 | 239.2 ± 76.7 | 261.2 ± 60.4 |

Drug Infusion vs Baseline: All comparisons NS

TABLE 6

SNRT and Wenckebach Cycle Length (WBK CL)

| | Baseline (msec) | Dose Level 1 Ave Δ (msec) | Dose Level 1 Ave Δ (%) | Dose Level 2 Ave Δ (msec) | Dose Level 2 Ave Δ (%) |
|---|---|---|---|---|---|
| SNRT (A1 600) | 986.0 ± 210.6 | 178.9 ± 248.9 | 22.8 ± 32.4 * | 78.0 ± 139.9 | 7.1 ± 14.4 |
| SNRT (A1 400) | 979.4 ± 223.6 | 78.8 ± 114.0 | 7.9 ± 13.4 | 122.9 ± 158.1 | 18.7 ± 33.2 * |
| WBK CL | 369.2 ± 90.4 | −13.1 ± 37.8 | −1.9 ± 7.4 | 17.5 ± 12.0 | 5.2 ± 3.7 * |

* Drug Infusion vs Baseline: p < 0.05 (wilcoxon)

TABLE 7

SNRT and Wenckebach Cycle Length (msec)

| | Baseline | Dose Level 1 | Dose Level 2 |
|---|---|---|---|
| SNRT (A1 600) | 986.0 ± 210.6 | 1157.8 ± 238.3 | 1033.3 ± 247.8 |
| SNRT (A1 400) | 979.4 ± 223.6 | 1114.4 ± 227.4 | 1047.1 ± 212.2 * |
| Wenckebach Cycle Length | 369.2 ± 90.4 | 388.1 ± 94.4 | 366.9 ± 53.7 * |

* Drug Infusion vs Baseline: p < 0.05 (wilcoxon)

TABLE 8

Atrial versus Ventricular Refractoriness

| (msec) | Baseline (msec) | Dose Level 1 Ave Δ (msec) | Dose Level 1 Ave Δ (%) | Dose Level 2 Ave Δ (msec) | Dose Level 2 Ave Δ (%) |
|---|---|---|---|---|---|
| AERP | | | | | |
| 600 | 204.4 ± 30.5 | 13.5 ± 14.4 | 6.9 ± 8.2 * | 31.4 ± 14.4 | 16.9 ± 9.0 * |
| 400 | 185.3 ± 30.0 | 5.0 ± 9.0 | 3.3 ± 5.4 | 24.4 ± 17.8 | 14.7 ± 11.5 * |
| 300 | 175.6 ± 27.2 | −3.1 ± 18.9 | −0.3 ± 10.9 | 21.1 ± 17.6 | 13.4 ± 11.8 * |

TABLE 8-continued

Atrial versus Ventricular Refractoriness

| (msec) | Baseline (msec) | Dose Level 1 Ave Δ (msec) | Dose Level 1 Ave Δ (%) | Dose Level 2 Ave Δ (msec) | Dose Level 2 Ave Δ (%) |
| --- | --- | --- | --- | --- | --- |
| VERP | | | | | |
| 600 | 254.1 ± 16.7 | 0.0 ± 10.0 | 0.0 ± 3.9 | 4.2 ± 14.6 | 1.8 ± 5.8 |
| 400 | 223.7 ± 17.6 | 1.7 ± 11.7 | 1.0 ± 4.9 | 4.4 ± 19.2 | 2.3 ± 8.5 |

* Drug Infusion vs Baseline: $p < 0.05$ (wilcoxon)

TABLE 9

Repolarization/Refractoriness

| | Baseline | Dose Level 1 | Dose Level 2 |
| --- | --- | --- | --- |
| AERP | | | |
| 600 msec | 204.4 ± 30.5 | 219.5 ± 32.2 * | 227.9 ± 22.5 * |
| 400 msec | 185.3 ± 30.0 | 195.0 ± 23.8 | 206.7 ± 25.6 * |
| 300 msec | 175.6 ± 27.2 | 180.5 ± 15.5 | 192.8 ± 20.2 * |
| VERP | | | |
| 600 msec | 254.1 ± 16.7 | 247.8 ± 22.0 | 261.7 ± 16.3 |
| 400 msec | 223.7 ± 17.6 | 226.7 ± 16.4 | 227.5 ± 16.3 |

* Drug Infusion vs Baseline: $p < 0.05$ (wilcoxon)

TABLE 10

ECG Intervals (400 msec)

| | Baseline (msec) | Dose Level 1 Ave Δ (msec) | Dose Level 1 Ave Δ (%) | Dose Level 2 Ave Δ (msec) | Dose Level 2 Ave Δ (%) |
| --- | --- | --- | --- | --- | --- |
| QRS | | | | | |
| A1 400 | 83.2 ± 6.6 | 1.6 ± 7.4 | 2.1 ± 8.5 | 7.3 ± 8.9 | 9.7 ± 11.4 |
| V1 400 | 145.7 ± 18.8 | 10.7 ± 15.4 | 7.6 ± 11.5 | 14.9 ± 15.2 | 10.3 ± 10.5 |
| QT | | | | | |
| A1 400 | 316.5 ± 26.2 | 12.6 ± 4.2 | 4.1 ± 1.4 | 30.3 ± 36.6 | 10.4 ± 11.7 |
| V1 400 | 368.5 ± 23.5 | 5.2 ± 14.3 | 1.4 ± 3.7 | 11.8 ± 24.8 | 3.2 ± 7.0 |

Drug Infusion vs Baseline: All comparisons NS

TABLE 11

ECG Intervals (400 msec)

| | Baseline | Dose Level 1 | Dose Level 2 |
| --- | --- | --- | --- |
| QRS | | | |
| A1 400 msec | 83.2 ± 6.6 | 87.0 ± 6.6 | 86.4 ± 9.0 |
| V1 400 msec | 145.7 ± 18.8 | 160.5 ± 23.0 | 157.3 ± 22.5 |
| QT | | | |
| A1 400 msec | 316.5 ± 26.2 | 325.4 ± 9.0 | 336.7 ± 27.8 |
| V1 400 msec | 368.5 ± 23.5 | 381.5 ± 25.2 | 376.3 ± 32.5 |

Drug Infusion vs Baseline: All comparisons NS

TABLE 12

ECG Intervals (600 msec)

| | Baseline | Dose Level 1 | Dose Level 2 |
| --- | --- | --- | --- |
| QRS | | | |
| A1 600 msec | 86 ± 7 | 89 ± 9 | 89 ± 8 |
| V1 600 msec | 157 ± 17 | 169 ± 24 | 157 ± 15 |
| QT | | | |
| A1 600 msec | 358 ± 21 | 363 ± 27 | 364 ± 20 |
| V1 600 msec | 415 ± 27 | 433 ± 30 | 412 ± 30 |

TABLE 13

Atrial MAP50

| MAP50 | Baseline | Dose Level 1 | Dose Level 2 |
| --- | --- | --- | --- |
| A1 600 msec | 155.8 ± 26.5 (n = 13) | 172.8 ± 31.9 (n = 9) | 165.5 ± 33.3 (n = 4) |
| A1 400 msec | 136.4 ± 34.3 (n = 13) | 152.6 ± 19.7 (n = 8) | 143.7 ± 25.2 (n = 6) |
| A1 300 msec | 137.3 ± 22.0 (n = 11) | 139.5 ± 20.4 (n = 8) | 135.6 ± 20.4 (n = 4) |
| A1 250 msec | 125.5 ± 25.5 (n = 10) | 134.2 ± 18.4 (n = 7) | 130.0 ± 14.5 (n = 3) |
| A1 200 msec | 100.5 ± 28.9 (n = 4) | 116.4 ± 15.4 (n = 2) | 124.0 (n = 1) |

Note:
Drug Infusion vs Baseline: all NS

TABLE 14

Correlation between Change in AERP 400 and End of Study
(T = 45) Plasma COMPOUND A Concentrations:

|  | Dose Level 1 | Dose Level 2 |
|---|---|---|
| Plasma Concentration of COMPOUND A (ng/ml) | 1084.3 ± 279.1 | 2173.8 ± 422.0 |
| AERP 400 (msec) Change from Baseline | 5.0 ± 9.0 | 24.4 ± 17.8 |
| Correlation | −0.068 | −0.057 |
| p value | NS (p > 0.05) | NS (p > 0.05) |

Adverse Effects:

There was one patient with transient hypotension resulting in a systolic blood pressure fall from 122 to 96 mm Hg, which was resolved in 5 minutes.

There were four patients with a transient tingling sensation.

There were three patients with a metallic taste in mouth and one patient with numbness in tongue.

Conclusion:

1. COMPOUND A dose-dependently prolongs atrial refractory periods.
2. COMPOUND A has a small but significant conduction slowing effect in the AV node, H is Purkinje, and ventricular tissue.
3. COMPOUND A at the doses studied had no significant effect on ventricular refractoriness, repolarization or conduction.

Example 2

Treatment of Acute Atrial Fibrillation

This was a randomized, double-blind, step-dose, placebo-controlled, parallel group study on humans. Fifty-six patients with atrial fibrillation of 3 to 72 h duration were randomized to one of two COMPOUND A dose groups or to placebo. The two COMPOUND A groups were RSD-1 (0.5 mg/kg followed by 1.0 mg/kg) or RSD-2 (2.0 mg/kg followed by 3.0 mg/kg), doses given by intravenous infusion over 10 min. The primary endpoint was termination of atrial fibrillation during a 10-min infusion or the subsequent 30-min. Secondary endpoints included the number of patients in sinus rhythm at 0.5, 1 and 24 h post-infusion and time to conversion to sinus rhythm. RSD-2 dose showed significant differences over placebo in: 1) termination of atrial fibrillation within 30-min 61% vs. 5%; p=0.0003); 2) patients in sinus rhythm at 30 min post-dose (56% vs. 5%; p=0.0008); 3) patients in sinus rhythm 1 h post-dose (53% vs. 5%; p=0.0014), and 4) median time to achieve conversion (14 vs. 162 min; p=0.016). COMPOUND A converted acute atrial fibrillation to sinus rhythm.

COMPOUND A is a mixed frequency-dependent $Na^+$ and atria-preferential $K^+$ channel blocker. In animal models of AF, COMPOUND A is effective in terminating and preventing relapse of AF. COMPOUND A selectively prolongs atrial refractory periods without significant effects on ventricular refractoriness or QT intervals.

Patients in this study had to have a rhythm of sustained atrial fibrillation (AF) with a duration of 3 to 72 h at the time of randomization. Patients were randomized to one of three groups and in each group received up to two 10-min intravenous infusions, separated by 30 min. Infusions were placebo followed by placebo, 0.5 mg/kg followed by 1.0 mg/kg COMPOUND A, or 2.0 mg followed by 3.0 mg COMPOUND A. The second dose in each group was administered only if AF was present 30 min after completion of the first dose. Doses for patients weighing>113 kg were capped as if the patient weight was 113 kg.

A Holter rhythm strip continuously monitored ECG, vital signs (blood pressure and heart rate, BP and HR, respectively) and $O_2$ saturation were recorded every 2 min from the start of infusion to 5 min after, as well as at 15, 30, 60, 120, 240, 360, and 480 min and at discharge and one-week follow-up. Twelve-lead ECGs were obtained before dosing and every minute during infusion to 5 min after, as well as at 15, 30, 60, 120, 240, 360, and 480 min and at discharge, 24 h and one-week follow-up, and at the time of arrhythmia termination or significant rhythm changes. Venous blood samples were drawn for COMPOUND A plasma concentrations at 0, 15, 30, 120, 240, 480 min discharge and at AF termination or significant adverse events.

Fifty-five patients were evaluated for efficacy. Data are presented as mean±SD, median with interquartile range (IQR), all tests were performed as two sided and 95% confidence interval (CI) were produced; p<0.05 was considered statistically significant unless stated otherwise. Analysis of the relationship between termination of AF and treatment was performed using a chi-square analysis. In cases of small cell frequencies, the Fisher's exact test was used. A Cochran-Armitage test statistic with table scores was used to test the ascending dose evaluation of efficacy.

The time to conversion from the start of the first infusion was analyzed by the Cox regression method of event time analysis and one-way ANOVA. Assessment of the significance of time point values and mean change from baseline to each follow-up reading of ECG intervals (QRS, QT, QTc), BP, and HR were made within dose groups using paired t tests, and comparisons among dose groups were made using a one-way ANOVA.

Demographic characteristics for all patients in the study are shown in Table 18.

TABLE 15

Demographic Characteristics for Patients in Each Study Group

|  |  | Placebo (n = 20) | COMPOUND A (0.5 and 1.0 mg/kg) (n = 18) | COMPOUND A (2.0 and 3.0 mg/kg) (n = 18) |
|---|---|---|---|---|
| Gender, n (%) | Male | 14 (70.0) | 10 (56) | 10 (56) |
| Age (yrs) | Median (range) | 64.0 (35-83) | 67.4 (24-85) | 60.8 (25-88) |
| Duration of AF (h) | Median (range) | 13.3 (5.1-59.4) | 11.5 (5.7-67.2) | 19.5 (5.1-70.4) |
| Previous AF history, n (%) |  | 75% | 61% | 44% |
| Lone AF (%) |  | 35% | 28% | 39% |
| Hypertension (%) |  | 45% | 72% | 56% |

TABLE 15-continued

Demographic Characteristics for Patients in Each Study Group

|  | Placebo (n = 20) | COMPOUND A (0.5 and 1.0 mg/kg) (n = 18) | COMPOUND A (2.0 and 3.0 mg/kg) (n = 18) |
|---|---|---|---|
| Diabetes (%) | 25% | 28% | 17% |
| Concomitant $\beta_1$-blocker (%) | 75% | 61% | 67% |
| Concomitant ACE - I (%) | 30% | 28% | 22% |
| Concomitant Dilt/verap (%) | 30% b | 22% | 33% |
| Concomitant digitalis (%) | 30% | 22% | 11% |

ACE-I = angiotensin converting enzyme-I; Dilt/verap = diltiazem/verapamil.

Baseline clinical characteristics were similar across groups except that patients in the placebo group tended to more frequently report AF in the past than in the COMPOUND A dosed groups.

FIG. 1 shows conversion efficacy, including cumulative percentage of patients terminating atrial fibrillation (AF) after infusions of placebo, 0.5 and 1 mg/kg COMPOUND A or 2.0 and 3.0 mg/kg COMPOUND A, in patients with recent onset AF. Efficacy was significantly higher after 2+3 mg/kg COMPOUND A than after placebo (p=0.0003) and was significantly different between the two COMPOUND A (p=0.0018) dosing regimens. The median time for termination of AF was 11 min from the start of the first infusion in the COMPOUND A treatment groups.

The cumulative AF termination within 30 min of infusion was 61% (11 of 18 patients) after 2+3 mg/kg COMPOUND A infusion, 11% (2 of 18 patients) after 0.5+1.0 mg/kg COMPOUND A and 5% (1 of 19 patients) after placebo+placebo. Paired comparisons indicated a statistically significant difference (p=0.0003) between placebo and the RSD-2 group. There was no significant difference in the success rates between the RSD-1 group and placebo. Of the 11 AF terminations in the RSD-2 group, eight terminated on the first infusion.

The number of patients in sinus rhythm at 30-min post-infusion was 56% (10 of 18 patients) in the RSD-2 group, 11% (2 of 18 patients) in the RSD-1 group and 5% (I of 19 patients) in the placebo group. The number of patients in sinus rhythm at 1 h post infusion was 53% (9 of 17 patients) in the RSD-2 group, 11% (2 of 18 patients) in the RSD-1 group, and 5% (1 of 19 patients) in the placebo group. Patients in sinus rhythm (excluding those electrically cardioverted) at 24 h post infusion was 79% (11 of 14 patients) in the RSD-2, 56% (5 of 9 patients) in the RSD-1 compared to 50% (5 of 10 patients) in the placebo group. Only the difference between RSD-2 and placebo was statistically significant at 30 min (p=0.008) and at 1 h (p=0.0014).

The median time to conversion to sinus rhythm from the start of the first infusion in the eleven responders in the RSD-2 group was 14 min (range, 3 to 871 min; p=0.016) compared to the five spontaneous responders in the placebo group with a median time of 162 min (range, 58 to 1119 min). The median time to conversion to sinus rhythm from the start of the first infusion in the five eventual responders in the RSD-1 group was 166 min (range, 1 to 332 min; p=0.886 vs. placebo).

The median time to termination of AF was 11 min after start of the first infusion (range, 3 to 58 min) in the RSD-2 group. In fact, all the responders in this group reached primary end-point during drug infusion or within 10 min of the last infusion. One of the eleven responders in this group converted from AF into atrial flutter and subsequently converted to sinus rhythm 14.5 h later.

Table 19 shows the ECG effects of COMPOUND A. Infusion of COMPOUND A did not significantly prolong QTc or QRS intervals compared to placebo. There was no difference in QT and QTc intervals between placebo (389±31 ms and 414±16 ms) and RSD-2 treatment (366±28 ms and 427±19 ms) using the first available ECG records after conversion to sinus rhythm.

TABLE 16

QTc and QRS Intervals and HR Values for Patients in Each Study Group

| Time Period | Placebo | COMPOUND A (0.5 and 1.0 mg/kg) | COMPOUND A (2.0 and 3.0 mg/kg) | P Value |
|---|---|---|---|---|
| QTC (MSEC) | | | | |
| Predrug baseline (n) | 20 | 16 | 17 | |
| mean ± SD | 424 ± 6 | 417 ± 6 | 434 ± 7 | 0.233 |
| End infusion 1 (n) | 19 | 17 | 17 | |
| mean ± SD | 430 ± 5 | 419 ± 6 | 449 ± 9 | 0.066 |
| End infusion 2 (n) | 16 | 17 | 11 | |
| mean ± SD | 436 ± 8 | 414 ± 11 | 447 ± 17 | 0.691 |
| QRS (MSEC) | | | | |
| Predrug baseline (n) | 20 | 17 | 18 | |
| mean ± SD | 87 ± 2 | 83 ± 3 | 86 ± 3 | 0.823 |
| End infusion 1 (n) | 19 | 17 | 17 | |
| mean ± SD | 89 ± 2 | 86 ± 3 | 95 ± 3 | 0.150 |
| End infusion 2 (n) | 16 | 17 | 11 | |
| mean ± SD | 88 ± 2 | 90 ± 6 | 99 ± 5 | 0.120 |

TABLE 16-continued

QTc and QRS Intervals and HR Values for Patients in Each Study Group

| Time Period | Placebo | COMPOUND A (0.5 and 1.0 mg/kg) | COMPOUND A (2.0 and 3.0 mg/kg) | P Value |
|---|---|---|---|---|
| HEART RATE (BPM) | | | | |
| Predrug baseline (n) | 20 | 16 | 17 | |
| mean ± SD | 112 ± 6 | 101 ± 6 | 108 ± 6 | 0.585 |
| End infusion 1 (n) | 19 | 17 | 17 | |
| mean ± SD | 115 ± 6 | 104 ± 7 | 98 ± 5 | 0.045 |
| End infusion 2 (n) | 16 | 17 | 11 | |
| mean ± SD | 109 ± 6 | 107 ± 6 | 104 ± 6 | 0.601 |

There were no statistically significant differences in ECG intervals after infusion between groups. Heart rate was decreased after 2 mg/kg COMPOUND A (p<0.05), reflecting the number of patients who converted to sinus rhythm in this group.

There were no clinically significant changes from baseline in systolic blood pressure, and there were no changes in blood pressures that were substantially different from those seen in the placebo group. There were two significant cases of hypotension reported in the placebo group and one mild case of transient hypotension in the RSD-2 group. Clinically significant treatment-related decreases in mean heart rate from baseline (mean: 106 beats per min) occurred in patients administered the RSD-2 dose, starting at $T_1=15$ min (mean: 90 beats per min). This likely reflected the conversion of several patients to normal sinus rhythm.

A total of thirty-nine patients experienced 122 adverse events over the course of the study, with a similar incidence of events among the three treatment groups. The majority of adverse events were of mild or moderate intensity. There were four mild adverse events that occurred in two patients considered either definitely or probably related to study drug. Both patients were in the RSD-2 dose group: one patient reported paraesthesia, and one patient reported paraesthesia, nausea, and hypotension.

The most common adverse events experienced in this study were cardiac disorders, reported by seven patients (35.0%) in the placebo group, four patients (22.2%) in the RSD-1 group, and three patients (16.7%) in the RSD-2 group. In addition to the serious adverse events discussed below, the cardiac disorders in the placebo group included two patients with non-sustained ventricular tachycardia and a patient with ventricular premature beats. Ventricular premature beats were also seen in two patients and sinus bradycardia in one patient of the low dose group. Ventricular premature beats were seen in two patients and sinus bradycardia in another patient in the RSD-2 group. Other adverse events occurring with a similar frequency among treatment groups were nervous system disorders, general disorders and infections.

Serious adverse events were reported in five patients (four in the placebo group and one in the RSD-1 group). A transient cerebral ischemic attack occurred 1 day after conversion in a placebo treated patient with a therapeutic international normalized ratio (INR) at the time of conversion. Severe bradycardia and hypotension immediately following conversion occurred in one patient, pulmonary edema in another patient and recurrent AF in the fourth placebo patient. One patient in the RSD-1 group experienced ventricular fibrillation, which was attributed to an asynchronous discharge during an electrical cardioversion attempt performed 1 h after receiving the second infusion.

Within the study period (24 h) electrical cardioversion was attempted in nine of 19 (47%) placebo treated, nine of 18 (50%) RSD-1 treated and four of 18 (22%) RSD-2 treated patients and was successful in eight (89%), nine (100%) and four (100%) patients, respectively.

Figure 2:
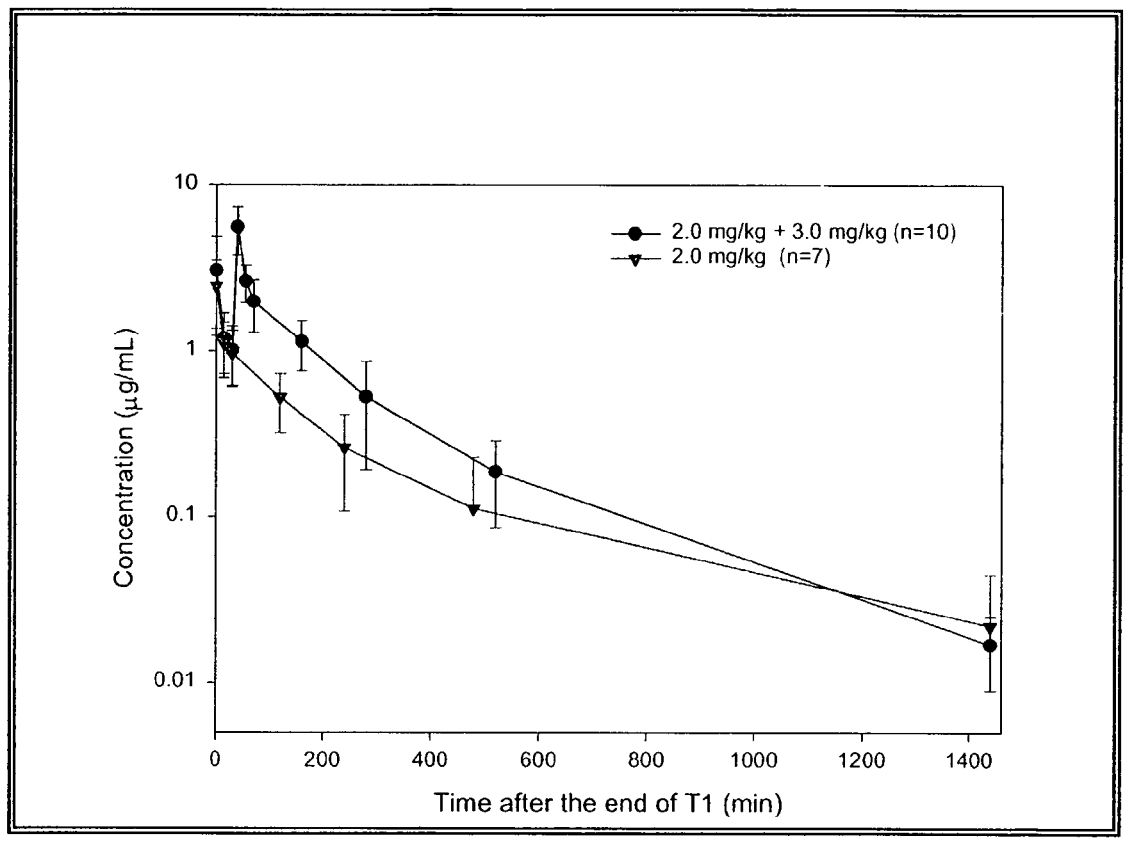
FIG. 2 shows the plasma concentrations of COMPOUND A after infusion in patients dosed at 2 mg/kg i.v. and those additionally dosed at 3 mg/kg i.v.

FIG. 2 shows a pharmacokinetic analysis of the data for COMPOUND A, and shows plasma concentrations of COMPOUND A after infusion in patients dosed at 2 mg/kg i.v. (filled inverted triangles) and those additionally dosed at 3 mg/kg i.v. (filled circles). COMPOUND A doses were infused over 10 min as indicated in the text. Initially a 2 mg/kg infusion was given and if required an additional 3 mg/kg was infused 30 min later in the RSD-2 group. Time is shown relative to the end of the first infusion (T1).

Mean peak COMPOUND A plasma levels were 5.8 μg/mL (range: 4.0 to 8.6 μg/mL) in the patients that received both the 2.0 and 3.0 mg/kg infusions of COMPOUND A and 1.9 μg/mL (range: 0.1 to 3.4 μg/mL) in those that received both 0.5 and 1.0 mg/kg COMPOUND A. Maximum plasma levels were seen at the end of the second infusion. Plasma drug levels at 24 h post-infusion were below the limit of detection (5 ng/mL) in the majority of patients who received RSD-1. Similarly, negligible plasma levels were seen at 24 h in the RSD-2 group; mean plasma levels were 0.017 μg/mL (range: <0.005 to 0.028 μg/mL). In those patients that received only the 2 mg/kg infusion, mean peak plasma levels at the end of infusion were 2.6 μg/mL (range: 1.4 to 4.5 μg/mL). The median plasma level at the time of AF conversion in these patients was 1.3 μg/mL (range: 1.1 to 3.5 μg/mL). The mean terminal elimination half life in these patients was 3.1 h (range: 1.7 to 5.4 h).

This study demonstrated that the upper dose of COMPOUND A (2+3 mg/kg) rapidly and effectively terminated AF compared to lower dose COMPOUND A and placebo. There were no serious adverse events associated with COMPOUND A, and observed SAEs were more common in the placebo group. In contrast to other antiarrhythmic drugs used for conversion of acute AF, there were no instances of drug related proarrhythmia. While these initial findings will require confirmation in larger scale clinical trials, this safety profile coupled with an efficacious and rapid onset confirms that COMPOUND A is a promising new agent for the medical conversion of acute AF.

COMPOUND A shows a higher net efficacy (61% to 5%=56%) for conversion of recent onset AF within 2 h of exposure.

This randomized controlled trial provides evidence for the efficacy of this atrial specific, $Na^+/K^+$ channel blocking agent for the treatment of AF. Intravenous COMPOUND A (2+3 mg/kg) was effective in rapidly terminating AF and was not associated with any drug induced proarrhythmia or any serious adverse event.

Example 3

Treatment of Recent Onset Acute Atrial Fibrillation

This study was conducted to assess the effectiveness and safety of COMPOUND A in the conversion of atrial fibrillation to sinus rhythm in humans.

The primary endpoint of this study was the proportion of patients with atrial fibrillation duration of 3 hours to 7 days who had treatment-induced conversion to sinus rhythm within 90 minutes of treatment. Secondary endpoints included the time-to-conversion of atrial fibrillation to sinus rhythm in patients with atrial fibrillation duration of 3 hours to 7 days; the proportion of patients with atrial fibrillation of 8 to 45 days who had treatment-induced conversion to sinus rhythm within 90 minutes of treatment, and the proportion of patients in the entire group with atrial fibrillation of 3 hours to 45 days who had treatment-induced conversion to sinus rhythm within 90 minutes of treatment.

336 patients were randomized in a 2:1 ratio of COMPOUND A to placebo (221 patients received COMPOUND A and 115 patients received placebo) and stratified by atrial fibrillation duration of 3 hours to 7 days and 8 to 45 days.

A first 10-minute infusion of a test compound (placebo or 3 mg/kg of COMPOUND A) was given to each patient. A second 10-minute infusion (placebo or 2 mg/kg of COMPOUND A) was given 15 minutes later if atrial fibrillation was not terminated. Safety was assessed by the incidence of adverse events, vital signs, laboratory data, ECG and holter monitoring.

The following Table 20 shows the effectiveness of COMPOUND A in the conversion of atrial fibrillation to sinus rhythm:

TABLE 17

Number of Patients Converted to Sinus Rhythm

| Treatment Group | Number of Patients (%) Converted to Sinus Rhythm | | |
|---|---|---|---|
| | 3 hr-7 days (n = 220) | 8-45 days (n = 116) | Entire Group 3 hr-45 days (n = 336) |
| COMPOUND A | 75 (52%)* | 6 (8%) | 83 (38%)* |
| Placebo | 3 (4%) | 0 (0%) | 3 (3%) |

*p < 0.001

Of the seventy-five patients receiving COMPOUND A in the 3 hours to 7 days group who converted to sinus rhythm within 90 minutes, the median time to conversion was eleven minutes. Of these patients, only one relapsed within 24 hrs of administration of the test compound. In the 30-day interval following the administration of the test compound, serious adverse events occurred in twenty-one patients (18%) in the placebo group and in twenty-nine patients (13%) in the COMPOUND A group, with the recurrence of atrial fibrillation being the most common (in fourteen patients (12%) in the placebo group and in thirteen patients (6%) in the COMPOUND A group. There were no cases of drug-related Torsades de Pointes. A transient alteration in taste was the most common non-cardiac side effect in the COMPOUND A group, occurring in sixty-six patients (30%), vs. one patient (0.9%) in the placebo group.

This study demonstrated that administration of COMPOUND A, in providing a rapid and high rate of conversion of atrial fibrillation to sinus rhythm, is a safe and effective method of treatment for recent onset atrial fibrillation.

Example 4

An Example Showing the Effect of Age, Gender, and Prior Rate Control Medications in the Treatment of Recent Onset Atrial Fibrillation in Humans with Compound A This experiment was designed to assess the effect of age, gender, and the use of rate control medications on the conversion of atrial fibrillation (AF) to sinus rhythm (SR) using a compound of the invention.

Patients (pts) were block randomized in a double-blind, controlled study in a 2:1 ratio to receive COMPOUND A or placebo, stratified by AF duration (3 hr-7 days; 8-45 days). COMPOUND A (3 mg/kg), or similar appearing placebo, were infused over 10-min, followed by a second infusion if AF was not terminated (2 mg/kg or placebo). The proportion of pts with AF duration 3 hr-7 days who had treatment-induced conversion to SR within 90 min was the primary endpoint. Logistic regression was used to examine the effect of age (<65 vs ≧65), gender, and a prior use of rate control medications (beta blockers, calcium antagonists, digoxin).

Overall, 220 pts were randomized in the primary end-point group: 145 received COMPOUND A and 75 received placebo. More patients converted to SR (52% vs 4%) upon treatment with COMPOUND A than in the placebo group (p<0.0001). Sub-grouping by age, gender, and the prior use of rate control drugs:

TABLE 18

Number of Patients Converted to Sinus Rhythm
Number of Pts (%) Converted to Sinus Rhythm: Subset with AF Duration 3 hr-7 days (n = 220)

| Treatment Group | Placebo | | COMPOUND A | |
|---|---|---|---|---|
| | Converted | n | Converted | n |
| <65 | 2 (4%) | 49 | 49 (56%) | 88 |
| ≧65 | 1 (4%) | 26 | 26 (46%) | 57 |
| Men | 2 (4%) | 48 | 53 (52%) | 102 |
| Women | 1 (4%) | 27 | 22 (51%) | 43 |
| Prior Rate Control Drugs | 3 (5%) | 67 | 56 (51%) | 109 |
| No Prior Rate Control Drugs | 0 (0%) | 8 | 19 (53%) | 36 |

Conversion to SR was statistically and clinically similar based on age, gender, and prior use of rate control medications. Moreover, no effect of these parameters on conversion was observed in the entire study group with AF duration 3 hr-45 days. The median time to conversion with COMPOUND A was 11 minutes in the 3 hr-7 day group (n=75). Overall, serious adverse events occurred in 21 (18%) placebo and 29 (13%) COMPOUND A pts 30 days following drug administration. No cases of drug-related Torsades de Pointes were recorded.

COMPOUND A is a safe and efficacious agent for the conversion of recent onset AF to SR. It appears to produce similar results in subgroups based on age, gender, and prior use of rate control medications.

Example 6

Atrial Arrhythmia Conversion Trial 1

This study was conducted to assess the efficacy and safety of COMPOUND A in the conversion of atrial fibrillation to sinus rhythm in humans. The study was a randomized, double-blind, placebo-controlled Phase III study.

Patients were randomized in a 2:1 ratio (COMPOUND A:placebo) and stratified by atrial fibrillation duration. The entire group of patients (pts) had atrial fibrillation duration from 3 hours to 45 days. One subgroup had atrial fibrillation duration from 3 hours to 7 days. Another subgroup had atrial fibrillation duration from 8 days to 45 days.

The primary endpoint of the study was the proportion of patients with atrial fibrillation duration of 3 hours to 7 days who had treatment-induced conversion of atrial fibrillation to sinus rhythm with 90 minutes. Secondary endpoints include the time-to-conversion of atrial fibrillation to sinus rhythm in patients with atrial fibrillation of 3 hours to 7 days and the proportion of patients with termination of atrial fibrillation within 90 minutes in the subgroup of patients with 8 days to 45 days of atrial fibrillation duration and in the entire group of patients with 3 hours to 45 days of atrial fibrillation duration.

Dosing was as follows: Placebo or 3.0 mg/kg of COMPOUND A was administered by infusion over a 10 minute period, followed by a 15-minute observation period. If atrial fibrillation was not terminated, placebo or 2.0 mg/kg of COMPOUND A was adminstered by infusion over a 10 minute period.

The patient population was randomized (n=356). 20 patients did not receive drug. There were 220 patients in the subgroup having 3 hours to 7 days atrial fibrillation. Of these 220 patients, 75 received placebo and 145 received COMPOUND A. There were 116 patients in the subgroup having 8 days to 45 days atrial fibrillation. Of these 116 patients, 40 received placebo and 76 received COMPOUND A.

The demographics of the entire patient population were as follows:

|  |  | Placebo n = 115 | COMPOUND A n = 221 | TOTAL n = 336 |
|---|---|---|---|---|
| Gender | Male | 75 (65%) | 159 (72%) | 234 (70%) |
| Age | Mean | 61.5 | 62.3 | 62.0 |
| Race | Caucasian | 113 (98%) | 212 (96%) | 325 (97%) |

The demographics of the subgroup of patients having 3 hours to 7 days atrial fibrillation were as follows:

|  |  | Placebo n = 75 | COMPOUND A n = 145 |
|---|---|---|---|
| Gender: | Male | 48 (64%) | 102 (70%) |
| Age: | Mean ± SD | 60 ± 12 | 60 ± 14 |
| Race: | Caucasian | 73 (97%) | 138 (95%) |
| Concomitant Therapy: | Beta Blockers | 72% | 64% |
|  | Ca Channel Blockers | 19% | 8%* |
|  | Class I AAD | 7% | 6% |
|  | Class III AAD | 4% | 5% |
|  | Digoxin | 30% | 24% |

*p > 0.05

The demographics of the patient population receiving placebo and the patient population receiving COMPOUND A with respect to median atrial fibrillation duration were as follows:

| Atrial Fibrillation Group | Placebo | COMPOUND A | TOTAL |
|---|---|---|---|
| 3 hrs - 7 days (n = 220) | 28 hours | 28 hours | 28 hours |
| 8 days - 45 days (n = 116) | 19 days | 26 days | 25 days |
| 3 hrs - 45 days (n = 336) | 42 hours | 59 hours |  |

Results:

For responders receiving COMPOUND A in the short duration subgroup (3 hrs-7 days atrial fibrillation), the median time to conversion was 11 minutes. For responders receiving COMPOUND A in the entire group (3 hrs-45 days atrial fibrillation), the median time to conversion was 11.5 minutes. 76% of the responders receiving COMPOUND A converted after the first dosing in both the short duration subgroup and the entire group.

In the COMPOUND A responders group, one patient relapsed into atrial fibrillation in the first 24 hours post-dosing. Cardioversion was attempted by other means in patients who did not respond in both the placebo and COMPOUND A groups as follows:

|  | Placebo n = 115 | COMPOUND A n = 221 | TOTAL n = 336 |
|---|---|---|---|
| Electrical cardioversion was attempted | 81 (70%) | 96 (43%) | 117 (53%) |
| Successfully converted | 74 (91%) | 82 (85%) | 156 (88%) |

The results of ventricular rhythms during the 24 hour period post-dosing (using a holter monitor) is as follows:

| Ventricular Rhythm >=5 beats, regardless of rhythm | Treatment Group | | |
|---|---|---|---|
|  | Placebo n = 115 | COMPOUND A n = 221 | TOTAL n = 336 |
| Total | 6 (5.2%) | 5 (2.3%) | 11 (3.3%) |
| Torsades de Pointes | 0 (0.0%) | 0 (0.0%) | 0 (0.0%) |
| Polymorphic sustained ventricular tachycardia | 0 (0.0%) | 0 (0.0%) | 0 (0.0%) |
| Polymorphic unsustained ventricular tachycardia | 0 (0.0%) | 0 (0.0%) | 0 (0.0%) |
| Monomorphic sustained ventricular tachycardia | 0 (0.0%) | 0 (0.0%) | 0 (0.0%) |
| Monomorphic unsustained ventricular tachycardia | 5 (4.3%) | 2 (0.9%) | 7 (2.1%) |
| Polymorphic unsustained aberrant condition | 0 (0.0%) | 0 (0.0%) | 0 (0.0%) |
| Monomorphic unsustained aberrant condition | 0 (0.0%) | 3 (1.4%) | 3 (0.9%) |
| Ventricular escape rhythm | 1 (0.9%) | 0 (0.0%) | 1 (0.3%) |

Figure 3:
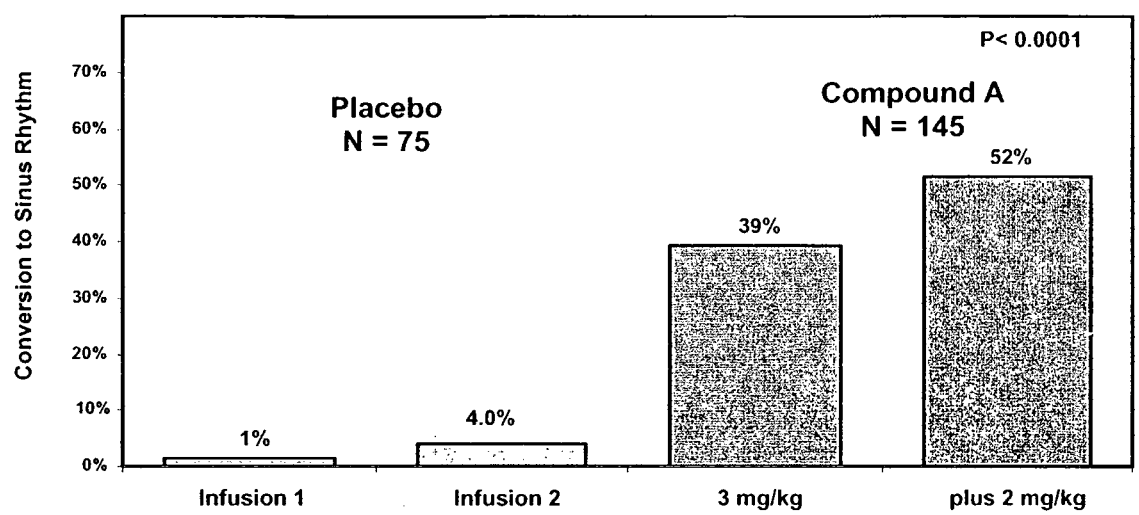
FIG. 3 shows the percentage of atrial fibrillation conversion to sinus rhythm in patients with AF of 3 hours to 7 days duration in a clinical trial.

The percentage of atrial fibrillation conversion to sinus rhythm in patients in the 3 hours to 7 days subgroup is shown in FIG. 3.

Figure 4:
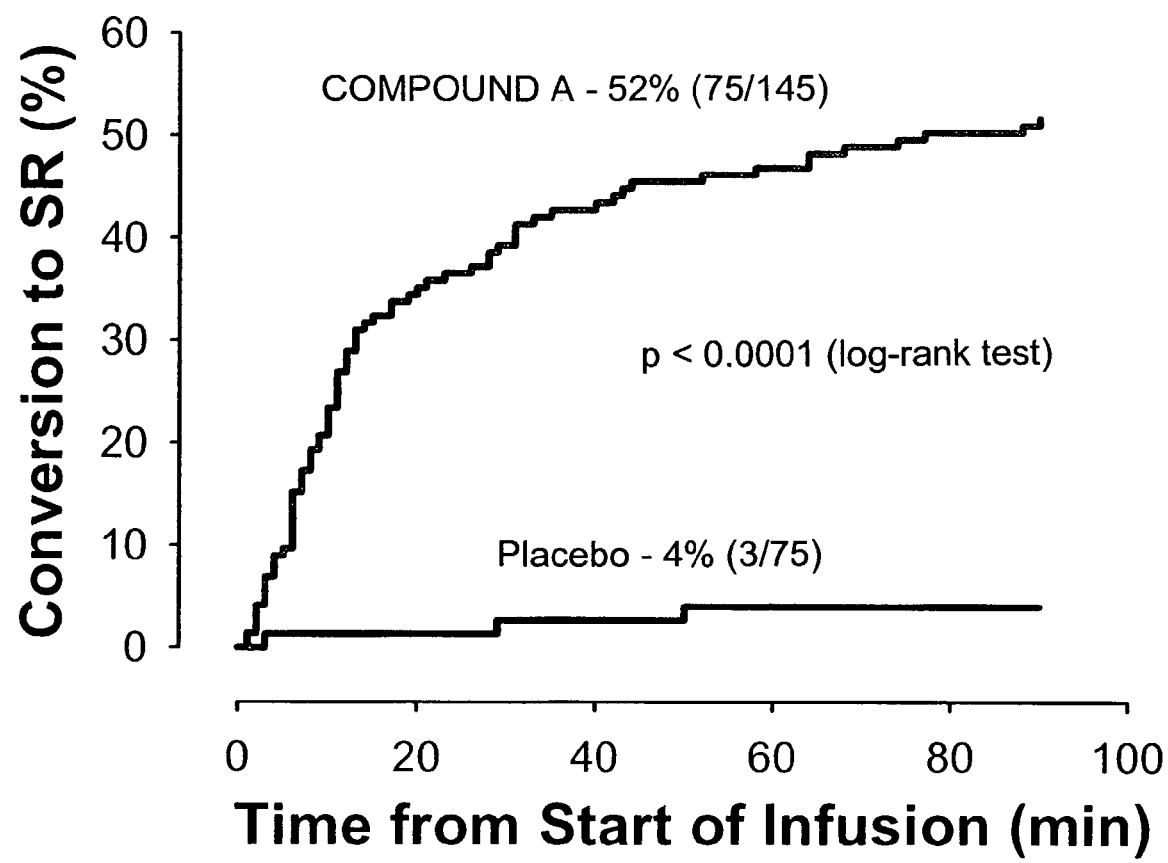
FIG. 4 shows the time course and percentage of patients with AF of 3 h to 7 days duration in a clinical trial that converted to sinus rhythm within 90 minutes.

The percentage of patients that converted to sinus rhythm within 90 minutes as a function of time in the 3 hours to 7 days subgroup is shown in FIG. 4.

Figure 5:
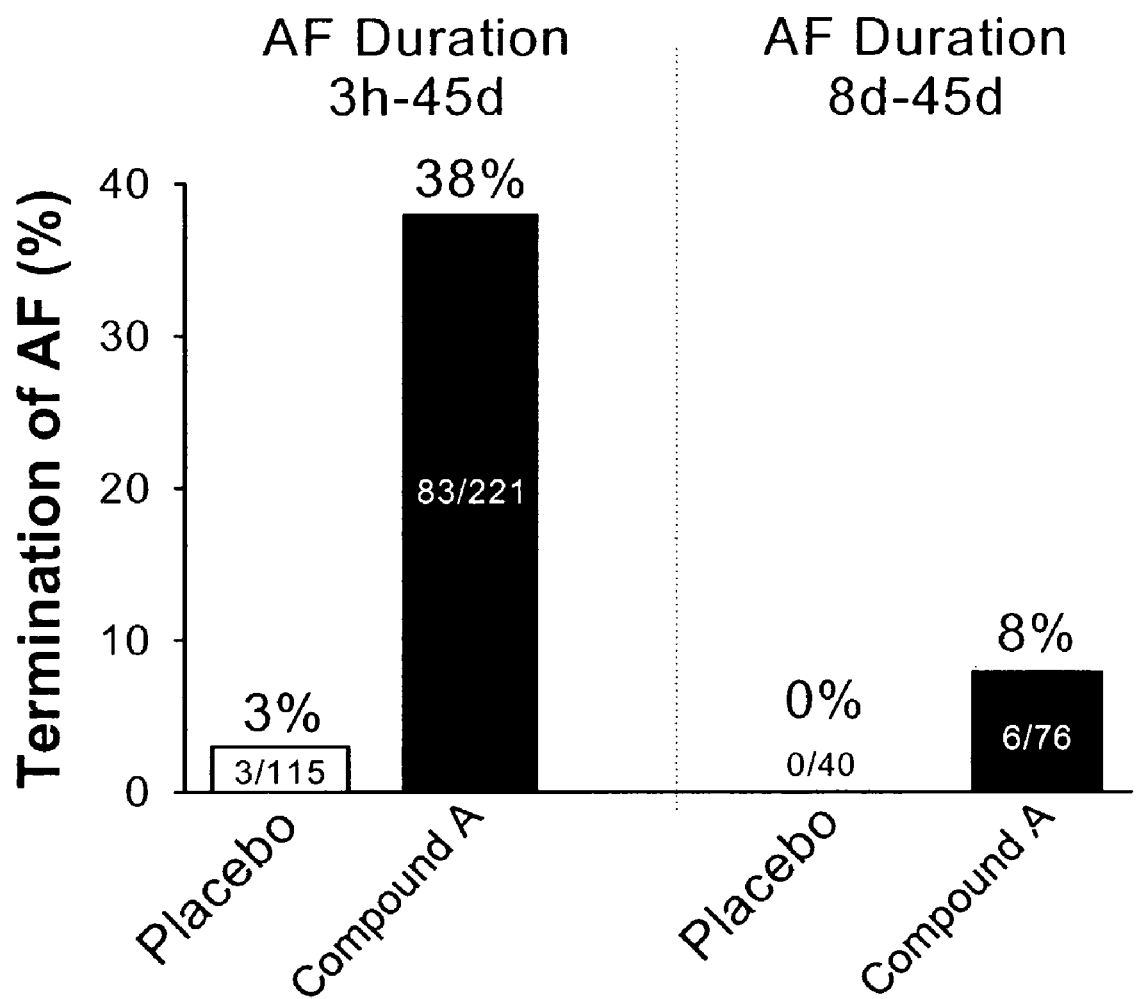
FIG. 5 shows the percentage of patients in a clinical trial whose atrial fibrillation terminated within 90 minutes.

The percentage of patients with atrial fibrillation duration in the entire patient population (3 hours to 45 days atrial fibrillation) and in the 8 days to 45 days subgroup whose atrial fibrillation terminated within 90 minutes is shown in FIG. 5 where p<0.0001 and p=0.092, respectively.

Figure 6:
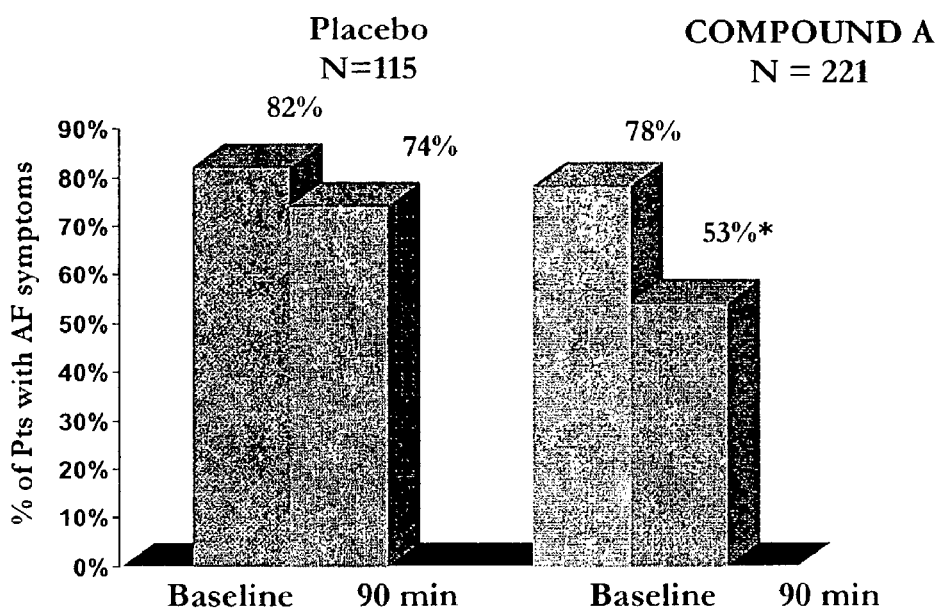
FIG. 6 shows atrial fibrillation symptom improvement at 90 minutes post-dosing in the subgroup of patients in a clinical trial.

Atrial fibrillation symptom improvement at 90 minutes post-dosing in the subgroup of patients having 3 hours to 45 days atrial fibrillation is shown in FIG. 6.

Figure 7:
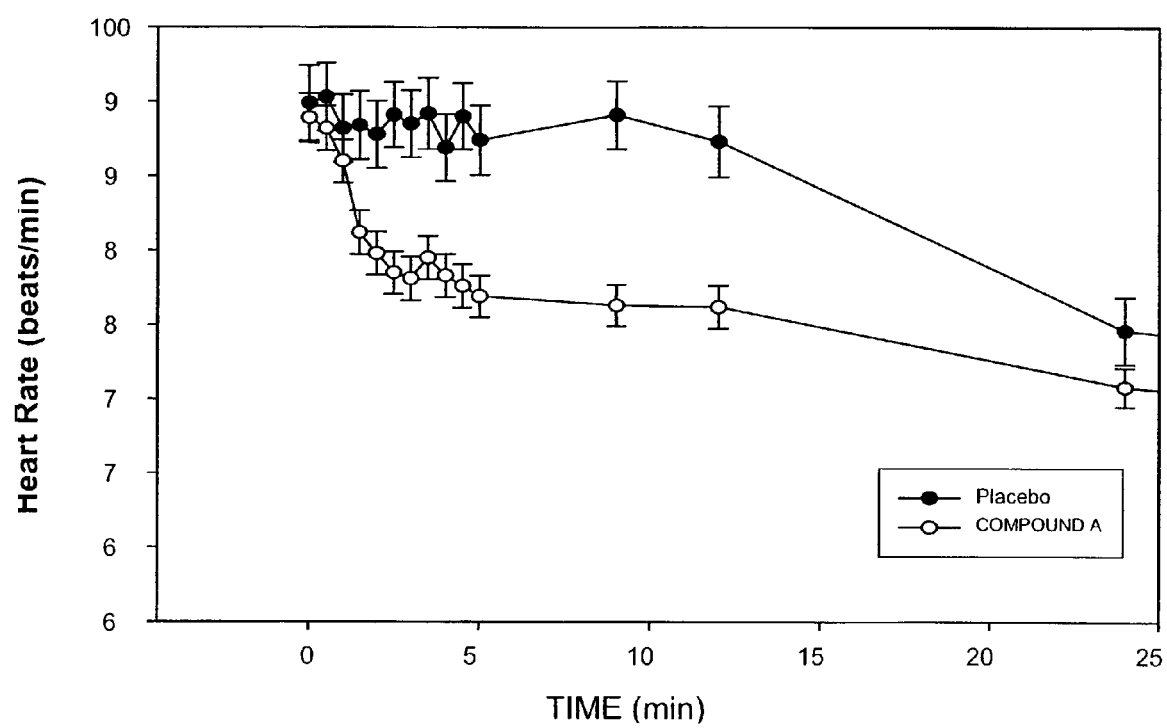
FIG. 7 shows the heart rate of patients in a clinical trial following dosing.

The heart rate of the patients in the entire group (n=336) following dosing is shown in FIG. 7.

Figure 8:
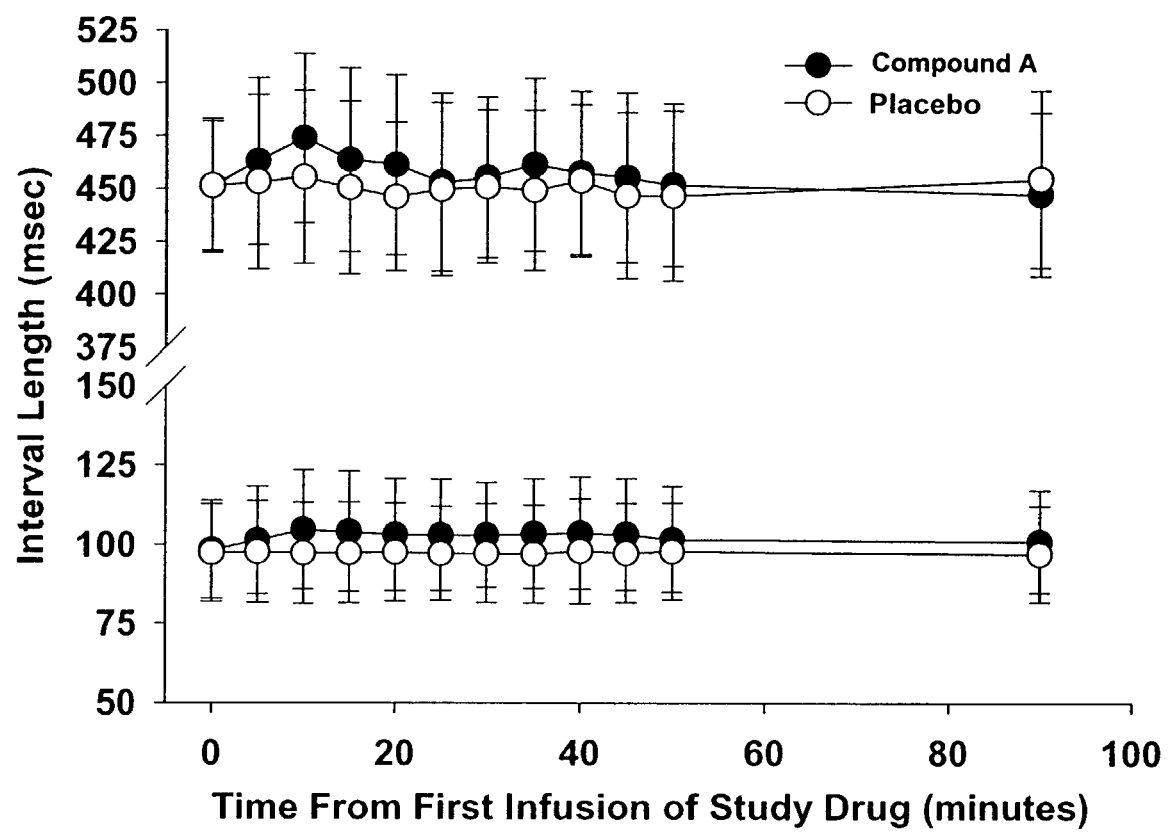
FIG. 8 shows the effect of the treatment on QRS and QTc intervals in patients in a clinical trial.

The effect of the treatment on QRS and QTc intervals as a function of time post first dosing in all patients (excluding those with pacemakers) is shown in FIG. 8.

Adverse Effects:

The incidence of the most common (≧5%) treatment-emergent adverse events during the 24 hour time period following dosing was as follows:

| System Organ Class | Preferred Term | Treatment Group | | |
|---|---|---|---|---|
| | | Placebo n = 115 | COMPOUND A n = 221 | TOTAL n = 336 |
| Cardiac disorders | Atrial fibrillation | 8 (7%) | 8 (4%) | 16 (5%) |
| Nervous system disorders | Dysgeusia | 1 (1%) | 66 (30%) | 67 (20%) |
| | Paraesthesia | 0 (0%) | 24 (11%) | 24 (7%) |
| GI disorders | Nausea | 1 (1%) | 20 (9%) | 21 (6%) |
| Respiratory, thoracic and mediastinal disorders | Cough | 1 (1%) | 11 (5%) | 12 (4%) |
| | Sneezing | 0 (0%) | 36 (16%) | 36 (11%) |
| Skin & subcutaneous disorders | Pruritus | 0 (0%) | 13 (6%) | 13 (4%) |
| Vascular disorders | Hypotension | 4 (4%) | 14 (6%) | 18 (5%) |

In the entire patient population (3 hrs to 45 days atrial fibrillation) incidence of serious adverse events during the 30-day follow-up period after dosing (≧1%) was as follows:

| System Organ Class | Treatment Group | | |
|---|---|---|---|
| | Placebo n = 115 | COMPOUND A n = 221 | TOTAL n = 336 |
| Total | 21 (18.3%) | 29 (13.1%) | 50 (14.9%) |
| Cardiac disorders | 17 (14.8%) | 22 (10.0%) | 39 (11.6%) |
| Infections and infestations | 0 (0.0%) | 3 (1.4%) | 3 (0.9%) |
| Nervous system disorders | 2 (1.7%) | 0 (0.0%) | 2 (0.6%) |
| Respiratory, thoracic and mediastinal disorders | 0 (0.0%) | 4 (1.8%) | 4 (1.2%) |
| Vascular disorders | 1 (0.9%) | 3 (1.4%) | 4 (1.2%) |

Plasma Levels:

Plasma levels were obtained, where possible, for the patients at various time intervals following the initial infusion. The time intervals were 10 minutes (i.e., immediately after the initial infusion), 35 minutes (i.e., immediately after the second infusion where applicable), 50 minutes, 90 minutes, and 24 hours. The following Table 24 shows measured plasma concentration data for the 150 patients that received both infusions of COMPOUND A. The data shown is the plasma concentration as determined at the 10 minute interval along with the maximum plasma concentration measured at any interval (N represents the number of patients that the data was ultimately based on).

TABLE 19

Plasma level data for patients receiving both infusions of COMPOUND A

| | Plasma Concentration of COMPOUND A at 10 min. (ng/mL) | Maximum Plasma Concentration of COMPOUND A (ng/mL) |
|---|---|---|
| N | 143 | 148 |
| Mean | 3907 | 4662 |
| Std. dev. | 1830 | 1543 |
| Median | 4070 | 4855 |
| Minimum | 0 | 1430 |
| Maximum | 9330 | 9330 |

The following Table 25 shows measured plasma concentration data for the 71 patients that received only a first infusion of Compound A. The data shown is the plasma concentration as determined at the 10 minute interval along with the maximum plasma concentration measured at any interval (N represents the number of patients that the data was ultimately based on).

TABLE 20

Plasma level data for patients receiving only a first infusion of COMPOUND A

| | Plasma Concentration of COMPOUND A at 10 min. (ng/mL) | Maximum Plasma Concentration of COMPOUND A (ng/mL) |
|---|---|---|
| N | 62 | 68 |
| Mean | 4275 | 4466 |
| Std. dev. | 2064 | 2565 |
| Median | 4075 | 4075 |
| Minimum | 0 | 7 |
| Maximum | 11600 | 11600 |

This study demonstrated that COMPOUND A is safe and effective for conversion of recent onset atrial fibrillation to sinus rhythm, that COMPOUND A demonstrates a rapid onset of action and that treatment with COMPOUND A did not affect subsequent electrical cardioversion.

What is claimed is:

1. A method of treating acute atrial fibrillation in a human, wherein the method comprises administering a therapeutically effective amount of an ion channel modulating compound in a pharmaceutically acceptable carrier to the human, wherein the ion channel modulating compound is a compound of formula (Ib):

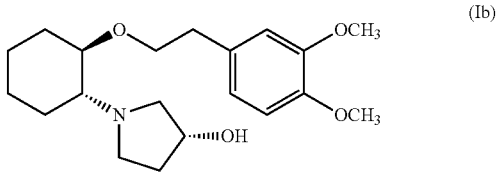

(Ib)

or a pharmaceutically acceptable salt thereof,
wherein the compound of formula (Ib) is administered in accordance with a dosage regimen comprising the following sequential steps:
a) administering over a first period of time a first dosage amount of 3.0 mg/kg to about 5.0 mg/kg of the compound of formula (Ib) to the human;

b) determining after a second period of time if the acute atrial fibrillation has terminated in the human;

c) if the acute atrial fibrillation has not terminated in the human after the second period of time, administering over a third period of time a second dosage amount of about 0.5 mg/kg to 2.0 mg/kg of the compound of formula (Ib) to the human; and d) optionally repeating step b) and c) until the acute atrial fibrillation has terminated, and wherein the first, second and any subsequent dosage amounts are administered parenterally.

2. The method of claim 1 wherein the dosage amount of the compound of formula (Ib) in step a) is 3.0 mg; kg and the dosage amount of the compound of formula (Ib) in step c) is 2.0 mg/kg.

3. The method of claim 1 wherein the first period of time is between about 5 and about 15 minutes, the second period of time is between 0 and about 15 minutes, and the third period of time is between about 5 and about 15 minutes.

4. The method of claim 1 wherein the first period of time is about 10 minutes, the second period of time is 15 minutes and the third period of time is about 10 minutes.

5. The method of claim 1 wherein the first dosage amount and the second dosage amount are both administered intravenously.

6. The method of claim 1 wherein the first, second and any subsequent dosage amounts are all administered intravenously.

7. The method of claim 1 wherein the compound of formula (I) is the hydrochloride salt of the compound of formula (Ib).

8. The method of claim 7 wherein the hydrochloride salt of the compound of formula (Ib) is administered in accordance with a dosage regimen comprising the following sequential steps:

a) intravenously administering over a first period of time of about 10 minutes a first dosage amount of 3.0 mg/kg of the hydrochloride salt of the compound of formula (Ib) to the human;

b) determining after a second period of time of about 15 minutes if the acute atrial fibrillation has terminated; and c) if the acute atrial fibrillation has not terminated in the human after the second period of time, administering over a third period of time of about 10 minutes a second dosage amount of 2.0 mg/kg of the hydrochloride salt of the compound of formula (Ib) to the human.

9. The method of claim 1 wherein the total dosage amount of the ion channel modulating compound administered to the human produces in the blood plasma of the human a maximum concentration of greater than about 0.1 µg/ml of the ion channel modulating compound.

10. The method of claim 9 wherein the maximum concentration is between about 0.3 µg/ml and about 20 µg/ml.

11. The method of claim 10 wherein the maximum concentration is less than about 12 µg/ml.

12. The method of claim 10 wherein the maximum concentration is about 4 µg/ml.

\* \* \* \* \*

UNITED STATES PATENT AND TRADEMARK OFFICE
CERTIFICATE OF CORRECTION

| | | Page 1 of 1 |
|---|---|---|
| PATENT NO. | : 8,263,638 B2 | |
| APPLICATION NO. | : 11/667139 | |
| DATED | : September 11, 2012 | |
| INVENTOR(S) | : Beatch et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 132 days.

Signed and Sealed this
Twenty-ninth Day of December, 2015

Michelle K. Lee
*Director of the United States Patent and Trademark Office*